(12) United States Patent
Yuying

(10) Patent No.: US 6,231,854 B1
(45) Date of Patent: *May 15, 2001

(54) METHIONINASE FORMULATIONS AND USE IN DIAGNOSTIC METHODS

(75) Inventor: Tan Yuying, San Diego, CA (US)

(73) Assignee: Anticancer, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/260,889

(22) Filed: Mar. 2, 1999

Related U.S. Application Data

(62) Continuation of application No. 08/914,377, filed on Aug. 19, 1997, now Pat. No. 5,888,506, which is a division of application No. 08/642,541, filed on May 3, 1996, now Pat. No. 5,891,704, which is a continuation-in-part of application No. 08/486,519, filed on Jun. 7, 1995, now Pat. No. 5,715,835, which is a continuation-in-part of application No. 08/424,300, filed as application No. PCT/US93/11311 on Nov. 19, 1993, now Pat. No. 5,690,929, which is a continuation-in-part of application No. 07/079,165, filed on Nov. 19, 1992.

(51) Int. Cl.[7] .............................. A61K 38/51; C12N 9/96; C12N 9/88
(52) U.S. Cl. ..................... 424/94.5; 424/94.2; 435/188; 435/232
(58) Field of Search .................................. 424/94.5, 94.2; 435/188, 232

(56) References Cited

FOREIGN PATENT DOCUMENTS

94/11535  5/1994 (WO) .
96/40284  12/1996 (WO) .

OTHER PUBLICATIONS

Kreis et al., *Cancer Research* (1973), 33:1862–1865.

Berezov, T.T. et al., "An improved prodcedure for isolation and purification of methionie gamma–lyase from *Pseudomonas putida*," Voprosy Meditsinskoi Khimii (1983), vol. 29, No. 4, pp. 131–135.*

Tan et al., "Overexpression and large–scale production of recombinant 1 –methionine–alpha–deamino–gamma– mercaptone than–lyase....", Protein Expression and Purification, vol. 9, No. 2, Mar. 1997, pp. 233–245.

Abstract, XP002092005 and JP 182592 A, Jul. 15, 1997.

Hiroyunki Inque et al., "Structural analysis of the L–methionine gamma–lyase gene from *Pseudominas putida*, ", *Journal of Biochemistry*, vol. 117, 1995, pp. 1120–1125.

* cited by examiner

*Primary Examiner*—Robert A. Wax
(74) *Attorney, Agent, or Firm*—Morrison & Foerster, LLP

(57) ABSTRACT

The present invention discloses the cloning of a methioninase-encoding nucleic acid molecule from *Pseudomonas putida* and the construction of high-level expression modules containing the methioninase-encoding nucleic acid molecule. The invention further provides expression modules that use the T7 RNA polymerase promoter to express the isolated methioninase-encoding nucleic acid molecules. Expression modules employing the T7 promoter were found to produce unexpectedly high levels of methioninase. The present invention further provides purification methods to obtain highly pure, endotoxin free methioninase, chemically modified forms of methioninase, crystallized methioninase and lyophilized methioninase preparations. The present invention further provides therapeutical methods using the disclosed recombinant methioninase preparations.

16 Claims, 22 Drawing Sheets

```
          10         20         30         40         50         60
           *          *          *          *          *          *
GCCGGTCTGT GGAATAAGCT TATAACAAAC CACAAGAGGC GGTTGCCATG CACGGCTCCA
CGGCCAGACA CCTTATTCGA ATATTGTTTG GTGTTCTCCG CCAACGGTAC GTGCCGAGGT
                                                  Met HisGlySer 70         80         90        100        110        120
           *          *          *          *          *          *
ACAAGCTCCC AGGATTTGCC ACCCGCGCCA TTCACCATGG CTACGACCCC CAGGACCACG
TGTTCGAGGG TCCTAAACGG TGGGCGCGGT AAGTGGTACC GATGCTGGGG GTCCTGGTGC
AsnLysLeuPro GlyPheAla ThrArgAla IleHisHisGly TyrAspPro GlnAspHis 130        140        150        160        170        180
           *          *          *          *          *          *
GCGGCGCACT GGTGCCACCG GTCTACCAGA CCGCGACGTT CACCTTCCCC ACCGTGGAAT
CGCCGCGTGA CCACGGTGGC CAGATGGTCT GGCGCTGCAA GTGGAAGGGG TGGCACCTTA
GlyGlyAlaLeu ValProPro ValTyrGln ThrAlaThrPhe ThrPhePro ThrValGlu 190        200        210        220        230        240
           *          *          *          *          *          *
ACGGCGCTGC GTGCTTTGCC GGCGAGCAGG CCGGCCATTT CTACAGCCGC ATCTCCAACC
TGCCGCGACG CACGAAACGG CCGCTCGTCC GGCCGGTAAA GATGTCGGCG TAGAGGTTGG
TyrGlyAlaAla CysPheAla GlyGluGln AlaGlyHisPhe TyrSerArg IleSerAsn 250        260        270        280        290        300
           *          *          *          *          *          *
CCACCCTCAA CCTGCTGGAA GCACGCATGG CCTCGCTGGA AGGCGGCGAG GCCGGGCTGG
GGTGGGAGTT GGACGACCTT CGTGCGTACC GGAGCGACCT TCCGCCGCTC CGGCCCGACC
ProThrLeuAsn LeuLeuGlu AlaArgMet AlaSerLeuGlu GlyGlyGlu AlaGlyLeu 310        320        330        340        350        360
           *          *          *          *          *          *
CGCTGGCCTC GGGCATGGGG GCGATCACGT CCACGCTATG GACACTGCTG CGCCCCGGTG
GCGACCGGAG CCCGTACCCC CGCTAGTGCA GGTGCGATAC CTGTGACGAC GCGGGGCCAC
AlaLeuAlaSer GlyMetGly AlaIleThr SerThrLeuTrp ThrLeuLeu ArgProGly
```

*FIG. 1A*

```
            370        380        390        400        410        420
             *    *     *    *     *    *     *    *     *    *     *    *
        ACGAGGTGCT GCTGGGCAAC ACCCTGTACG GCTGCACCTT TGCCTTCCTG CACCACGGCA
        TGCTCCACGA CGACCCGTTG TGGGACATGC CGACGTGGAA ACGGAAGGAC GTGGTGCCGT
        AspGluValLeu LeuGlyAsn ThrLeuTyr GlyCysThrPhe AlaPheLeu HisHisGly 430        440        450        460        470        480
             *    *     *    *     *    *     *    *     *    *     *    *
        TCGGCGAGTT CGGGGTCAAG CTGCGCCATG TGGACATGGC CGACCTGCAG GCACTGGAGG
        AGCCGCTCAA GCCCCAGTTC GACGCGGTAC ACCTGTACCG GCTGGACGTC CGTGACCTCC
        IleGlyGluPhe GlyValLys LeuArgHis ValAspMetAla AspLeuGln AlaLeuGlu 490        500        510        520        530        540
             *    *     *    *     *    *     *    *     *    *     *    *
        CGGCCATGAC GCCGGCCACC CGGGTGATCT ATTTCGAGTC GCCGGCCAAC CCCAACATGC
        GCCGGTACTG CGGCCGGTGG GCCCACTAGA TAAAGCTCAG CGGCCGGTTG GGGTTGTACG
        AlaAlaMetThr ProAlaThr TrpValIle TyrPheGluSer ProAlaAsn ProAsnMet 550        560        570        580        590        600
             *    *     *    *     *    *     *    *     *    *     *    *
        ACATGGCCGA TATCGCCGGC GTGGCGAAGA TTGCACGCAA GCACGGCGCG ACCGTGGTGG
        TGTACCGGCT ATAGCGGCCG CACCGCTTCT AACGTGCGTT CGTGCCGCGC TGGCACCACC
        HisMetAlaAsp IleAlaGly ValAlaLys IleAlaArgLys HisGlyAla ThrValVal 610        620        630        640        650        660
             *    *     *    *     *    *     *    *     *    *     *    *
        TCGACAACAC CTACTGCACG CCGTACCTGC AACGGCCACT GGAGCTGGGC GCCGACCTGG
        AGCTGTTGTG GATGACGTGC GGCATGGACG TTGCCGGTGA CCTCGACCCG CGGCTGGACC
        ValAspAsnThr TyrCysThr ProTyrLeu GlnTrpProLeu GluLeuGly AlaAspLeu 670        680        690        700        710        720
             *    *     *    *     *    *     *    *     *    *     *    *
        TGGTGCATTC GGCCACCAAG TACCTGAGCG GCCATGGCGA CATCACTGCT GGCATTGTGG
        ACCACGTAAG CCGGTGGTTC ATGGACTCGC CGGTACCGCT GTAGTGACGA CCGTAACACC
        ValValHisSer AlaThrLys TyrLeuSer GlyHisGlyAsp IleThrAla GlyIleVal
```

FIG. 1B

```
              730        740        750        760        770        780
               *  *       *  *       *  *       *  *       *  *       *  *
          TGGGCAGCCA GGCACTGGTG GACCGTATAC GTCTGCAGGG CCTCAAGGAC ATGACCGGTG
          ACCCGTCGGT CCGTGACCAC CTGGCATATG CAGACGTCCC GGAGTTCCTG TACTGGCCAC
          ValGlySerGln AlaLeuVal AspArgIle ArgLeuGlnGly LeuLysAsp MetThrGly 790        800        810        820        830        840
               *  *       *  *       *  *       *  *       *  *       *  *
          CGGTGCTCTC GCCCCATGAC GCCGCACTGT TGATGCGCGG CATCAAGACC CTCAACCTGC
          GCCACGAGAG CGGGGTACTG CGGCGTGACA ACTACGCGCC GTAGTTCTGG GAGTTGGACG
          AlaValLeuSer ProHisAsp AlaAlaLeu LeuMetArgGly IleLysThr LeuAsnLeu 850        860        870        880        890        900
               *  *       *  *       *  *       *  *       *  *       *  *
          GCATGGACCG CCACTGCGCC AACGCTCAGG TGCTGGCCGA GTTCCTCGCC CGGCAGCCGC
          CGTACCTGGC GGTGACGCGG TTGCGAGTCC ACGACCGGCT CAAGGAGCGG GCCGTCGGCG
          ArgMetAspArg HisCysAla AsnAlaGln ValLeuAlaGlu PheLeuAla TrpGlnPro 910        920        930        940        950        960
               *  *       *  *       *  *       *  *       *  *       *  *
          AGGTGGAGCT GATCCATTAC CCGGGCCTGG CGAGCTTCCC GCAGTACACC CTGGCCCGCC
          TCCACCTCGA CTAGGTAATG GGCCCGGACC GCTCGAAGGG CGTCATGTGG GACCGGGCGG
          GlnValGluLeu IleHisTyr ProGlyLeu AlaSerPhePro GlnTyrThr LeuAlaArg 970        980        990       1000       1010       1020
               *  *       *  *       *  *       *  *       *  *       *  *
          AGCAGATGAG CCAGCCGGGC GGCATGATCG CCTTCGAACT CAAGGGCGGC ATCGGTGCCG
          TCGTCTACTC GGTCGGCCCG CCGTACTAGC GGAAGCTTGA GTTCCCGCCG TAGCCACGGC
          GlnGlnMetSer GlnProGly GlyMetIle AlaPheGluLeu LysGlyGly IleGlyAla 1030       1040       1050       1060       1070       1080
               *  *       *  *       *  *       *  *       *  *       *  *
          GGCGGCGGTT CATGAACGCC CTGCAACTGT TCAGCCGCGC GGTGAGCCTG GGCGATGCCG
          CCGCCGCCAA GTACTTGCGG GACGTTGACA AGTCGGCGCG CCACTCGGAC CCGCTACGGC
          GlyTrpTrpPhe MetAsnAla LeuGlnLeu PheSerArgAla ValSerLeu GlyAspAla
```

FIG. 1C

```
           1090        1100        1110        1120        1130        1140
            *   *       *   *       *   *       *   *       *   *       *   *
          AGTCGCTGGC GCAGCACCCG GCAAGCATGA CTCATTCCAG CTATACCCCA GAGGAGCGTG
          TCAGCGACCG CGTCGTGGGC CGTTCGTACT GAGTAAGGTC GATATGGGGT CTCCTCGCAC
          GluSerLeuAla GlnHisPro AlaSerMet ThrHisSerSer TyrThrPro GluGluArg 1150        1160        1170        1180        1190        1200
            *   *       *   *       *   *       *   *       *   *       *   *
          CGCATTACGG CATCTCCGAG GGGCTGGTGC GGTTGTCGGT GGGGCTGGAA GACATCGACG
          GCGTAATGCC GTAGAGGCTC CCCGACCACG CCAACAGCCA CCCCGACCTT CTGTAGCTGC
          AlaHisTyrGly IleSerGlu GlyLeuVal TrpLeuSerVal GlyLeuGlu AspIleAsp 1210        1220        1230        1240        1250        1260
            *   *       *   *       *   *       *   *       *   *       *   *
          ACCTGCTGGC CGATGTGCAA CAGGCACTCA AGGCGAGTGC CTGAACCCGT CACGGATGAG
          TGGACGACCG GCTACACGTT GTCCGTGAGT TCCGCTCACG GACTTGGGCA GTGCCTACTC
          AspLeuLeuAla AspValGln GlnAlaLeu LysAlaSerAla 1270        1280        1290        1300        1310        1320
            *   *       *   *       *   *       *   *       *   *       *   *
          GTCAATGCAA TGGTGGCAAT GATGAACCTT GTGCCTGGCG ACGGCGTGCC CGGTGACAGC
          CAGTTACGTT ACCACCGTTA CTACTTGGAA CACGGACCGC TGCCGCACGG GCCACTGTCG 1330        1340        1350        1360
            *   *       *   *       *   *       *   *       *
          GACCCTGGCG AAACTGCAGA GTGGCTGGAG GCGCTGGAGT CGACCCTGG
          CTGGGACCGC TTTGACGTCT CACCGACCTC CGCGACCTCA GCTGGGACC
```

FIG. 1D

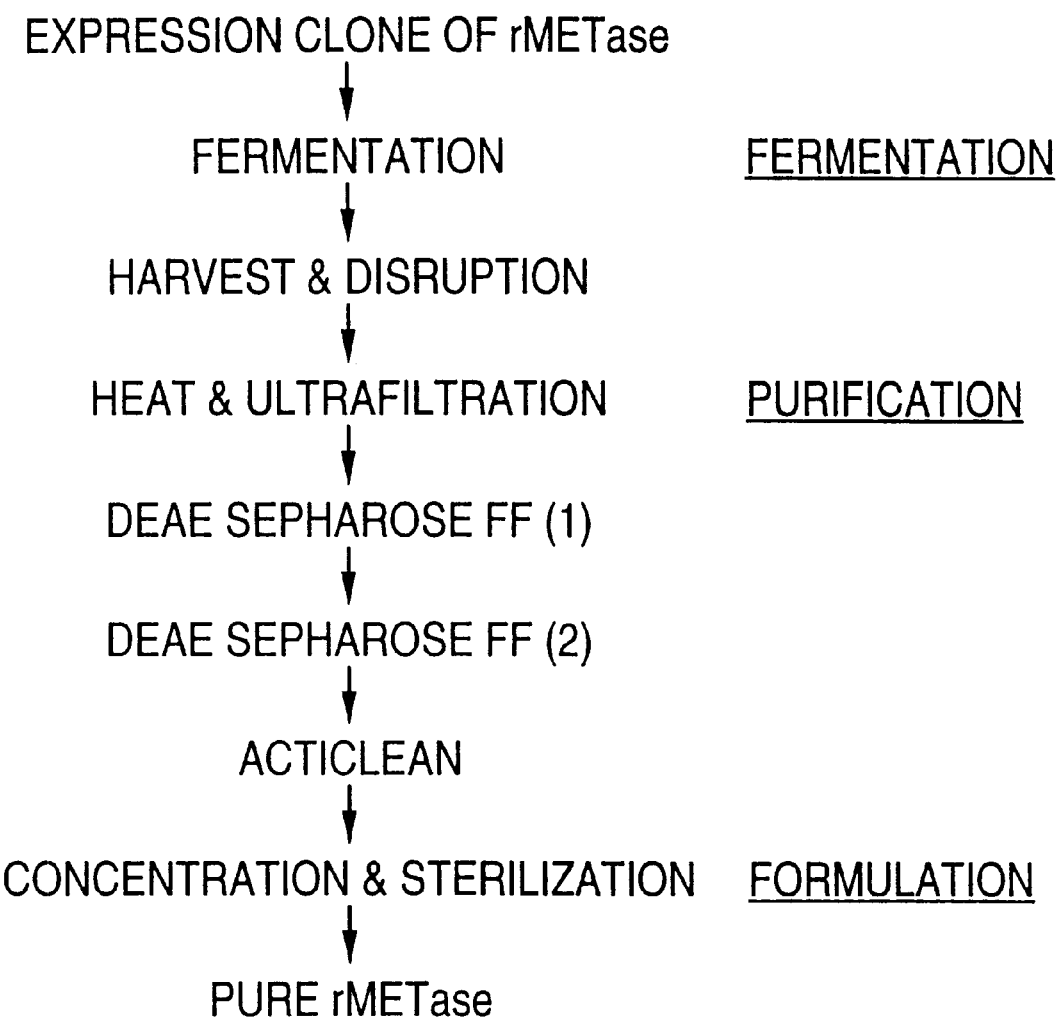

FIG. 3

PURIFICATION OF rMETase (pAC-1 CLONE)

| PROCEDURE (BATCH 11) | VOLUME (ml) | ACTIVITY (units) | PROTEIN (g) | SA* (units/mg) | RECOVERY RATE (%) | YIELD (%) |
|---|---|---|---|---|---|---|
| CELL LYSIS | 5,000 | 82,000 | 29.3 | 2.8 | 100 | 100 |
| HEAT & UF** | 4,500 | 77,000 | 19.3 | 4.0 | 94 | 94 |
| DEAE-FF.1 | 2,200 | 65,400 | 6.0 | 10.9 | 85 | 80 |
| DEAE-FF.2 | 800 | 57,500 | 2.88 | 20.0 | 88 | 70 |
| ACTICLEAN & CONCENTRATION | 182 | 52,000 | 2.59 | 20.1 | 90 | 63 |

* S.A.: SPECIFIC ACTIVITY.   ** UF: ULTRAFILTRATION

1. NATIVE METHIONINASE
2. MOLECULAR WEIGHT MARKERS
3. RECOMBINANT METHIONINASE

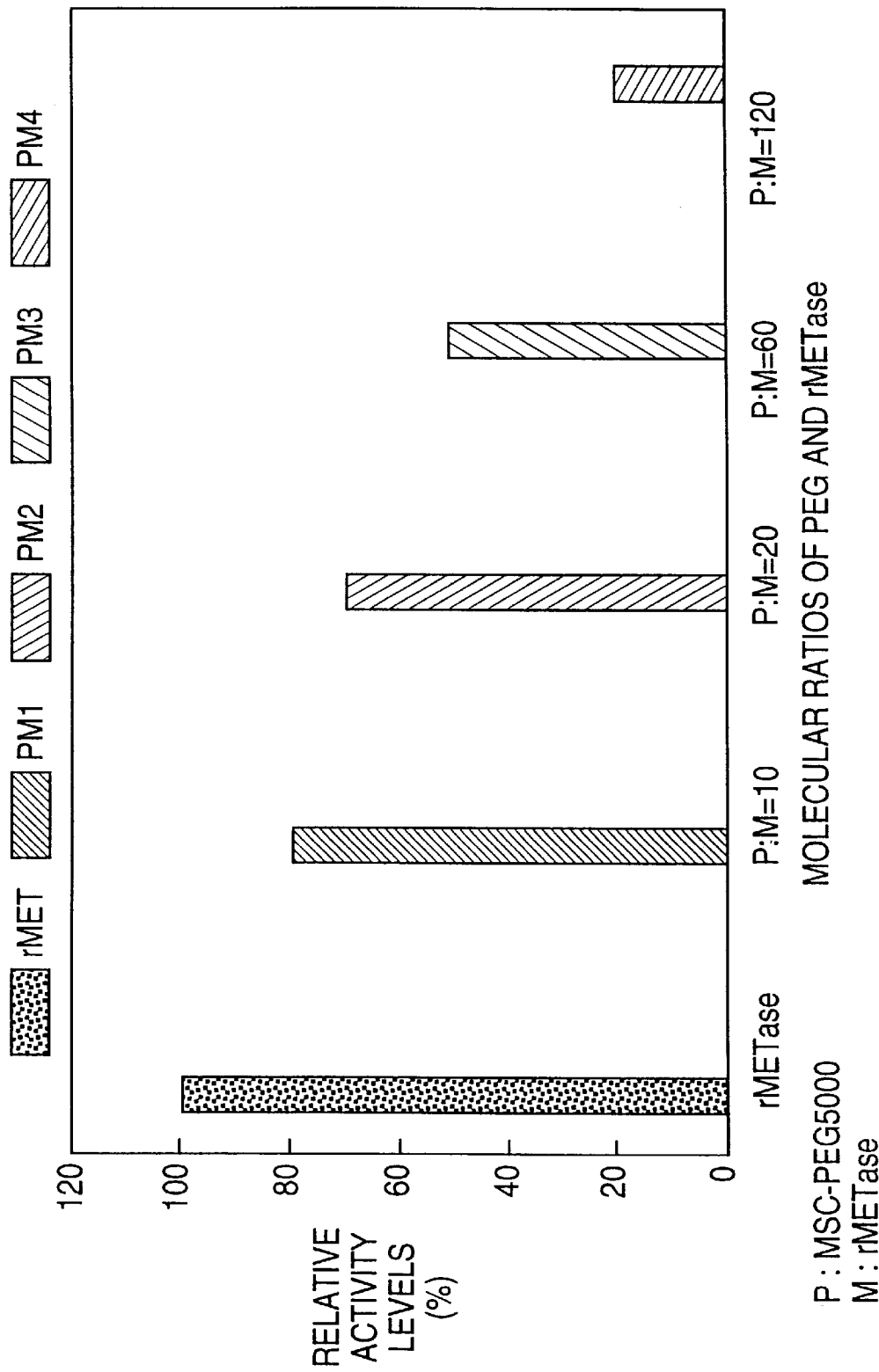

FIG. 18

TOXICITY OF METHIONINASE
(CLINICAL PHASE I TRIAL)

| PHYSICAL & LABORATORY EXAMINATION | GRADE | | |
|---|---|---|---|
| | PATIENT 1 | PATIENT 2 | PATIENT 3 |
| HEMATOLOGICAL | 0 | 0 | 0 |
| GASTROINTESTINAL | 0 | 0 | 0 |
| RENAL | 0 | 0 | 0 |
| PULMONARY | 0 | 0 | 0 |
| FEVER | 0 | 0 | 0 |
| ALLERGIC | 0 | 0 | 0 |
| PHLEBITIS | 0 | 0 | 0 |
| CUTANEOUS | 0 | 0 | 0 |
| CARDIAC | 0 | 0 | 0 |
| NEUROLOGICAL | 0 | 0 | 0 |

* ACCORDING TO WHO TOXICITY CRITERIA

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1369 base pairs
      (B) TYPE: nucleic acid
      (C) STRANDEDNESS: double
      (D) TOPOLOGY: linear (ii) MOLECULE TYPE: Genomic DNA (iv) ANTI-SENSE: NO (ix) FEATURE:
      (A) NAME/KEY: Coding Sequence
      (B) LOCATION: 48...1241
      (D) OTHER INFORMATION:

(xi) SEQUENCE DESCRIPTION: SEQ ID NO:1:

```
GCCGGTCTGT GGAATAAGCT TATAACAAAC CACAAGAGGC GGTTGCC ATG CAC GGC        56
                                                  Met His Gly
                                                    1

TCC AAC AAG CTC CCA GGA TTT GCC ACC CGC GCC ATT CAC CAT GGC TAC       104
Ser Asn Lys Leu Pro Gly Phe Ala Thr Arg Ala Ile His His Gly Tyr
  5                  10                  15

GAC CCC CAG GAC CAC GGC GGC GCA CTG GTG CCA CCG GTC TAC CAG ACC       152
Asp Pro Gln Asp His Gly Gly Ala Leu Val Pro Pro Val Tyr Gln Thr
 20                  25                  30                  35
```

```
GCG ACG TTC ACC TTC CCC ACC GTG GAA TAC GGC GCT GCG TGC TTT GCC      200
Ala Thr Phe Thr Phe Pro Thr Val Glu Tyr Gly Ala Ala Cys Phe Ala
            40                  45                  50

GGC GAG CAG GCC GGC CAT TTC TAC AGC CGC ATC TCC AAC CCC ACC CTC      248
Gly Glu Gln Ala Gly His Phe Tyr Ser Arg Ile Ser Asn Pro Thr Leu
        55                  60                  65

AAC CTG CTG GAA GCA CGC ATG GCC TCG CTG GAA GGC GGC GAG GCC GGG      296
Asn Leu Leu Glu Ala Arg Met Ala Ser Leu Glu Gly Gly Glu Ala Gly
            70                  75                  80

CTG GCG CTG GCC TCG GGC ATG GGG GCG ATC ACG TCC ACG CTA TGG ACA      344
Leu Ala Leu Ala Ser Gly Met Gly Ala Ile Thr Ser Thr Leu Trp Thr
        85                  90                  95

CTG CTG CGC CCC GGT GAC GAG GTG CTG CTG GGC AAC ACC CTG TAC GGC      392
Leu Leu Arg Pro Gly Asp Glu Val Leu Leu Gly Asn Thr Leu Tyr Gly
100                 105                 110                 115

TGC ACC TTT GCC TTC CTG CAC CAC GGC ATC GGC GAG TTC GGG GTC AAG      440
Cys Thr Phe Ala Phe Leu His His Gly Ile Gly Glu Phe Gly Val Lys
                120                 125                 130

CTG CGC CAT GTG GAC ATG GCC GAC CTG CAG GCA CTG GAG GCG GCC ATG      488
Leu Arg His Val Asp Met Ala Asp Leu Gln Ala Leu Glu Ala Ala Met
            135                 140                 145

ACG CCG GCC ACC CGG GTG ATC TAT TTC GAG TCG CCG GCC AAC CCC AAC      536
Thr Pro Ala Thr Arg Val Ile Tyr Phe Glu Ser Pro Ala Asn Pro Asn
        150                 155                 160

ATG CAC ATG GCC GAT ATC GCC GGC GTG GCG AAG ATT GCA CGC AAG CAC      584
Met His Met Ala Asp Ile Ala Gly Val Ala Lys Ile Ala Arg Lys His
            165                 170                 175

GGC GCG ACC GTG GTG GTC GAC AAC ACC TAC TGC ACG CCG TAC CTG CAA      632
Gly Ala Thr Val Val Val Asp Asn Thr Tyr Cys Thr Pro Tyr Leu Gln
180                 185                 190                 195

CGG CCA CTG GAG CTG GGC GCC GAC CTG GTG GTG CAT TCG GCC ACC AAG      680
Arg Pro Leu Glu Leu Gly Ala Asp Leu Val Val His Ser Ala Thr Lys
                200                 205                 210

TAC CTG AGC GGC CAT GGC GAC ATC ACT GCT GGC ATT GTG GTG GGC AGC      728
Tyr Leu Ser Gly His Gly Asp Ile Thr Ala Gly Ile Val Val Gly Ser
            215                 220                 225

CAG GCA CTG GTG GAC CGT ATA CGT CTG CAG GGC CTC AAG GAC ATG ACC      776
Gln Ala Leu Val Asp Arg Ile Arg Leu Gln Gly Leu Lys Asp Met Thr
        230                 235                 240

GGT GCG GTG CTC TCG CCC CAT GAC GCC GCA CTG TTG ATG CGC GGC ATC      824
Gly Ala Val Leu Ser Pro His Asp Ala Ala Leu Leu Met Arg Gly Ile
            245                 250                 255

AAG ACC CTC AAC CTG CGC ATG GAC CGC CAC TGC GCC AAC GCT CAG GTG      872
Lys Thr Leu Asn Leu Arg Met Asp Arg His Cys Ala Asn Ala Gln Val
260                 265                 270                 275

CTG GCC GAG TTC CTC GCC CGG CAG CCG CAG GTG GAG CTG ATC CAT TAC      920
Leu Ala Glu Phe Leu Ala Arg Gln Pro Gln Val Glu Leu Ile His Tyr
                280                 285                 290

CCG GGC CTG GCG AGC TTC CCG CAG TAC ACC CTG GCC CGC CAG CAG ATG      968
Pro Gly Leu Ala Ser Phe Pro Gln Tyr Thr Leu Ala Arg Gln Gln Met
            295                 300                 305

AGC CAG CCG GGC GGC ATG ATC GCC TTC GAA CTC AAG GGC GGC ATC GGT     1016
Ser Gln Pro Gly Gly Met Ile Ala Phe Glu Leu Lys Gly Gly Ile Gly
        310                 315                 320

GCC GGG CGG CGG TTC ATG AAC GCC CTG CAA CTG TTC AGC CGC GCG GTG     1064
Ala Gly Arg Arg Phe Met Asn Ala Leu Gln Leu Phe Ser Arg Ala Val
            325                 330                 335

AGC CTG GGC GAT GCC GAG TCG CTG GCG CAG CAC CCG GCA AGC ATG ACT     1112
Ser Leu Gly Asp Ala Glu Ser Leu Ala Gln His Pro Ala Ser Met Thr
```

-continued

```
340              345              350              355
CAT TCC AGC TAT ACC CCA GAG GAG CGT GCG CAT TAC GGC ATC TCC GAG         1160
His Ser Ser Tyr Thr Pro Glu Glu Arg Ala His Tyr Gly Ile Ser Glu
            360              365              370

GGG CTG GTG CGG TTG TCG GTG GGG CTG GAA GAC ATC GAC GAC CTG CTG         1208
Gly Leu Val Arg Leu Ser Val Gly Leu Glu Asp Ile Asp Asp Leu Leu
            375              380              385

GCC GAT GTG CAA CAG GCA CTC AAG GCG AGT GCC TGAACCCGTC ACGGATGAGG      1261
Ala Asp Val Gln Gln Ala Leu Lys Ala Ser Ala
            390              395

TCAATGCAAT GGTGGCAATG ATGAACCTTG TGCCTGGCGA CGGCGTGCCC GGTGACAGCG      1321

ACCCTGGCGA AACTGCAGAG TGGCTGGAGG CGCTGGAGTC GACCCTGG                   1369
```

(2) INFORMATION FOR SEQ ID NO:2:

(i) SEQUENCE CHARACTERISTICS:
        (A) LENGTH: 398 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met His Gly Ser Asn Lys Leu Pro Gly Phe Ala Thr Arg Ala Ile His
 1               5                  10                  15

His Gly Tyr Asp Pro Gln Asp His Gly Gly Ala Leu Val Pro Pro Val
                20                  25                  30

Tyr Gln Thr Ala Thr Phe Thr Phe Pro Thr Val Glu Tyr Gly Ala Ala
            35                  40                  45

Cys Phe Ala Gly Glu Gln Ala Gly His Phe Tyr Ser Arg Ile Ser Asn
50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
            100                 105                 110

Leu Tyr Gly Cys Thr Phe Ala Phe Leu His His Gly Ile Gly Glu Phe
        115                 120                 125

Gly Val Lys Leu Arg His Val Asp Met Ala Asp Leu Gln Ala Leu Glu
    130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
            180                 185                 190

Tyr Leu Gln Arg Pro Leu Glu Leu Gly Ala Asp Leu Val Val His Ser
        195                 200                 205

Ala Thr Lys Tyr Leu Ser Gly His Gly Asp Ile Thr Ala Gly Ile Val
    210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
```

```
                245                 250                 255
Arg Gly Ile Lys Thr Leu Asn Leu Arg Met Asp Arg His Cys Ala Asn
            260                 265                 270

Ala Gln Val Leu Ala Glu Phe Leu Ala Arg Gln Pro Gln Val Glu Leu
        275                 280                 285

Ile His Tyr Pro Gly Leu Ala Ser Phe Pro Gln Tyr Thr Leu Ala Arg
    290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
            340                 345                 350

Ser Met Thr His Ser Ser Tyr Thr Pro Glu Glu Arg Ala His Tyr Gly
        355                 360                 365

Ile Ser Glu Gly Leu Val Arg Leu Ser Val Gly Leu Glu Asp Ile Asp
    370                 375                 380

Asp Leu Leu Ala Asp Val Gln Gln Ala Leu Lys Ala Ser Ala
385                 390                 395
```

(2) INFORMATION FOR SEQ ID NO:3:

(i) SEQUENCE CHARACTERISTICS:
        (A) LENGTH: 1369 base pairs
        (B) TYPE: nucleic acid
        (C) STRANDEDNESS: single
        (D) TOPOLOGY: linear (ii) MOLECULE TYPE: Genomic DNA (iv) ANTI-SENSE: YES (xi) SEQUENCE DESCRIPTION: SEQ ID NO:3:

```
CCAGGGTCGA CTCCAGCGCC TCCAGCCACT CTGCAGTTTC GCCAGGGTCG CTGTCACCGG     60
GCACGCCGTC GCCAGGCACA AGGTTCATCA TTGCCACCAT TGCATTGACC TCATCCGTGA    120
CGGGTTCAGG CACTCGCCTT GAGTGCCTGT TGCACATCGG CCAGCAGGTC GTCGATGTCT    180
TCCAGCCCCA CCGACAACCG CACCAGCCCC TCGGAGATGC CGTAATGCGC ACGCTCCTCT    240
GGGGTATAGC TGGAATGAGT CATGCTTGCC GGGTGCTGCG CCAGCGACTC GGCATCGCCC    300
AGGCTCACCG CGCGGCTGAA CAGTTGCAGG GCGTTCATGA ACCGCCGCCC GGCACCGATG    360
CCGCCCTTGA GTTCGAAGGC GATCATGCCG CCCGGCTGGC TCATCTGCTG GCGGGCCAGG    420
GTGTACTGCG GGAAGCTCGC CAGGCCCGGG TAATGGATCA GCTCCACCTG CGGCTGCCGG    480
GCGAGGAACT CGGCCAGCAC CTGAGCGTTG GCGCAGTGGC GGTCCATGCG CAGGTTGAGG    540
GTCTTGATGC CGCGCATCAA CAGTGCGGCG TCATGGGGCG AGAGCACCGC ACCGGTCATG    600
TCCTTGAGGC CCTGCAGACG TATACGGTCC ACCAGTGCCT GGCTGCCCAC CACAATGCCA    660
GCAGTGATGT CGCCATGGCC GCTCAGGTAC TTGGTGGCCG AATGCACCAC CAGGTCGGCG    720
CCCAGCTCCA GTGGCCGTTG CAGGTACGGC GTGCAGTAGG TGTTGTCGAC CACCACGGTC    780
GCGCCGTGCT TGCGTGCAAT CTTCGCCACG CCGGCGATAT CGGCCATGTG CATGTTGGGG    840
TTGGCCGGCG ACTCGAAATA GATCACCCGG GTGGCCGGCG TCATGGCCGC CTCCAGTGCC    900
TGCAGGTCGG CCATGTCCAC ATGGCGCAGC TTGACCCCGA ACTCGCCGAT GCCGTGGTGC    960
AGGAAGGCAA AGGTGCAGCC GTACAGGGTG TTGCCCAGCA GCACCTCGTC ACCGGGGCGC   1020
AGCAGTGTCC ATAGCGTGGA CGTGATCGCC CCCATGCCCG AGGCCAGCGC CAGCCCGGCC   1080
```

TCGCCGCCTT CCAGCGAGGC CATGCGTGCT TCCAGCAGGT TGAGGGTGGG GTTGGAGATG        1140

CGGCTGTAGA AATGGCCGGC CTGCTCGCCG GCAAAGCACG CAGCGCCGTA TTCCACGGTG        1200

GGGAAGGTGA ACGTCGCGGT CTGGTAGACC GGTGGCACCA GTGCGCCGCC GTGGTCCTGG        1260

GGGTCGTAGC CATGGTGAAT GGCGCGGGTG GCAAATCCTG GGAGCTTGTT GGAGCCGTGC        1320

ATGGCAACCG CCTCTTGTGG TTTGTTATAA GCTTATTCCA CAGACCGGC                   1369

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:4:

GCCGGTCTGT GGAATAAGCT                                                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:5:

CCAGGGTCGA CTCCAGCGCC                                                    20

(2) INFORMATION FOR SEQ ID NO:6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iv) ANTI-SENSE: NO (xi) SEQUENCE DESCRIPTION: SEQ ID NO:6:

GGAATTCCAT ATGCACGGCT CCAACAAGC                                          29

(2) INFORMATION FOR SEQ ID NO:7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (iv) ANTI-SENSE: YES (xi) SEQUENCE DESCRIPTION: SEQ ID NO:7:

AGTCATCCTA GGTCACATCA TCATCATCAT CATGGCACTC GCCTTGAGTG C                 51

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear -continued

```
        (iv) ANTI-SENSE: YES (xi) SEQUENCE DESCRIPTION: SEQ ID NO:8:

AGTCATCCTA GGTCAGGCAC TCGCCTTGAG TGC                                    33
```

METHIONINASE FORMULATIONS AND USE IN DIAGNOSTIC METHODS

RELATED APPLICATIONS

This application is a continuation of U.S. Ser. No. 08/914,377 filed Aug. 19, 1997, now U.S. Pat. No. 5,888,506, which application is a divisional of application Ser. No. 08/642,541 filed May 3, 1996 now allowed, which is a continuation-in-part of U.S. Ser. No. 08/486,519 filed Jun. 7, 1995, now U.S. Pat. No. 5,715,835; which is a continuation-in-part of U.S. Ser. No. 08/424,300 filed Apr. 24, 1995 and now U.S. Pat. No. 5,690,929 which application was the National Phase of the PCT application No. PCT/US93/11311 filed Nov. 19, 1993, which was a continuation-in-part of U.S. Ser. No. 07/079,165 filed Nov. 19, 1992. The contents of these document is incorporated herein by reference.

TECHNICAL FIELD

The present invention relates to expression modules that encode and express high levels of recombinant methioninase, recombinant methioninase produced using high-level expression modules, compositions containing recombinant methioninase produced using high-level expression modules, methods for purifying recombinant methioninase produced using high-level expression modules, chemically modified forms of recombinant methioninase, and methods of using recombinant methioninase produced using high-level expression modules in anti-methionine and antihomocysteine therapy.

BACKGROUND

Therapeutic drug-based treatment of cancer is directed at the use of medicinals which selectively inhibit or kill the cancer cells while not harming normal tissue function beyond acceptable amounts. The difficulty with conventional chemotherapy has been the toxicity of therapeutic drugs for normal tissue.

Many tumors have been shown to have absolute requirement for methionine in a variety of cell types and evaluated tumor tissues, including tumors of the colon, breast prostate, ovary, kidney, larynx melanoma, sarcoma, lung, brain, stomach and bladder as well as leukemias and lymphomas. Methionine dependence has been defined as an inability of tumors to grow when methionine is replaced by homocysteine in the growth medium. See, for example, Chello et al., *Cancer Res.*, 33:1898–1904, 1973; and Hoffman, *Anticancer Res.*, 5:1–30, 1985.

Methionine depletion has been shown to selectively synchronize methionine-dependent tumor cells into late $S/G_2$ phase of the cell cycle. Hoffman et al, *Proc. Natl. Acad. Sci. USA*, 12:7306–7310, 1980. Using the combination of methionine deprivation, followed by repletion of methionine coupled with exposure to an antimitotic agent, termed anti-methionine chemotherapy, tumor cells have been selectively eliminated from cocultures of normal and tumor cells, resulting in cultures of normal cells proliferating vigorously. Stern et al., *J. Natl. Cancer Inst.*, 76:629–639, 1986.

However, in order for methionine-dependent chemotherapy to, be conducted in vivo, it is necessary to have a means to effectively deplete serum of circulating methionine. Methionine depletion methods have not been described that reduce circulating methionine levels in vivo in a manner sufficient to be effective in antitumor therapies.

Methioninase, an enzyme which degrades methionine, has been purified from a variety of bacterial sources, and has been reported to slow the rate of tumor cell proliferation in vitro. Kreis et al., *Cancer Res.*, 33:1862–1865, and 1866–1869, 1973; Tanaka et al., *FEBS Letters*, 66:307–311 1976; Ito et al., *J. Biochem.* 79:1263–1272, 1976; and Nakayama et al., *Agric. Biol. Chem.* 48:2367–2369, 1984.

Kreis et al., *Cancer Res.* 33:1866–1869, 1973, have described the use of highly impure methioninase preparations isolated from *Clostridium sporgenes* at 1150 units/kg/day to inhibit growth of carcinosarcoma cells implanted in a mouse model. Although the enzyme apparently reduced primary tumor cell growth, it was not reported to reduce the T/C (treated versus control) ratio of tumor diameter below 50%, and was not reported to have any effect on metastasis. The authors also indicated that tumor specificity of the methioninase cannot be expected without other unspecified interventions, and further do not comment on the possibly that endotoxin, or other components of the impure preparation, were responsible for the effects observed. The only toxicity studies, reported were absence of animal body weight loss after the duration of the treatment, and negative gross examination for toxicity. Further, the authors report that the enzyme had a serum half life of 4 hours.

Kreis et al., *Cancer Res.* 33:1866–1869, 1973, further reported the use of a methionine-free diet as a means to deplete methionine as an antitumor therapy. However, the authors reported that the diet did not slow tumor growth as effectively as the use of an impure preparation of methioninase and resulted in the undesirable side effect of continuous loss of weight of the animal. The authors did not report the use of methionine deficient diets combined with methioninase treatment, and did not study cell synchronization.

The priority applications of the present invention disclose effective chemotherapy of tumors directed at effectively reducing the amount of methionine as to provide a beneficial antitumor effect without deleterious injury using methioninase. The present invention improves the disclosed therapeutic and diagnostic methods and composition by providing a source for producing commercially viable quantities of highly pure recombinant methioninase.

BRIEF DESCRIPTION OF THE INVENTION

The present invention is based, in part, on the generation of high-level expression modules encoding methioninase. The expression modules of the present invention produce recombinant methioninase in an appropriate host cell, such as *E. coli*, at levels ranging from about 5–75% of total cellular protein.

Based on this observation, the invention provides high expression modules encoding methioninase that expresses unexpectedly high levels of recombinant methioninase. High expression modules, such as those utilizing the T7 RNA polymerase promoter, have been used to produce recombinant methioninase at about 1 to 4 gram/liter with a specific activity of about 2 to 4 units/mg, before purification, using appropriate incubation conditions and purification methods.

The invention further provides methods of accurately selecting transformants containing high-level expression modules encoding methioninase for the ability to produce high levels of recombinant methioninase. Such procedures can be used to specifically select transformants containing recombinant methioninase-encoding DNA molecules isolated from an organism that naturally produces methioninase, as well as to identify transformants that express altered forms of a recombinant methioninase-encoding DNA molecule that increases the level of expression in a given host or the activity of the recombinant methioninase produced.

The invention further provides methods of producing recombinant methioninase using cells containing high-level expression modules encoding methioninase. The present invention further provides methods of purifying methioninase to obtain a highly pure, endotoxin free methioninase.

The invention further provides substantially pure recombinant methioninase produced using cells containing high-level expression modules encoding methioninase.

The present invention further provides methioninase in crystallized form.

The invention further provides compositions for diagnostic and therapeutic use that contain recombinant methioninase produced using a high-level expression module encoding methioninase.

The invention further provides methods for inhibiting tumor cell growth using the recombinant methioninase of the present invention.

The invention further provides the recombinant methioninase, of the present invention in chemically modified forms, such as by coupling of the recombinant methioninase to polymers such as polyethylene glycol (PEG).

The recombinant methioninase of the present invention can further be used to lower homocysteine levels in patients to reduce the risk of, and to treat, cardiovascular diseases.

The recombinant methioninase of the present invention can further be used to deplete methionine for tumor diagnosis and imaging.

Other features, advantages and related embodiments of the present invention will be apparent based on the disclosures contained herein.

BRIEF DESCRIPTION OF THE DRAWINGS

FIGS. 1A–1D, provides the nucleotide (and corresponding amino acid sequence) of a methioninase encoding DNA molecule isolated from P. putida.

FIG. 2 provides an outline of the purification steps used to obtain highly pure, endotoxin free methioninase.

FIG. 3 provides an overview of typical purity and recovery yields for rMETase.

FIG. 7 provides typical activity data for PEG-rMETase.

FIG. 18 provides a toxicity evaluation of methioninase in a human patients.

Figure 4A:
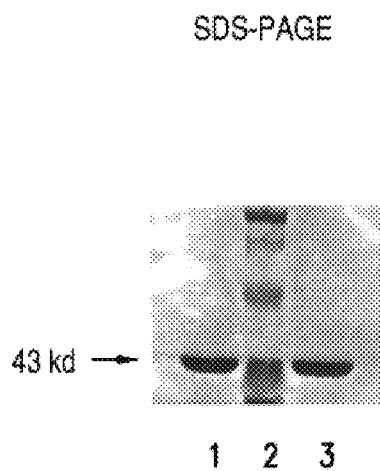
FIGS. 4A–4B provides an example of the purity of rMETase produce by the present methods.

The drawings are not necessarily to scale, and certain features of the invention may be exaggerated in scale and shown in schematic form in the interest of clarity and conciseness.

DESCRIPTION OF THE INVENTION

A. Definitions

"Amino acid residue" refers to an amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. NH2 refers to the free amino group present at the amino terminus of a polypeptide. COOH refers to the free carboxy group present at the carboxy terminus of a polypeptide. In keeping with standard polypeptide nomenclature (described in J. Biol. Chem. 243:3552–59, 1969, and adopted at 37 CFR 1.822(b)(2)), hereby incorporated by reference.

| TABLE OF CORRESPONDENCE | | |
|---|---|---|
| SYMBOL | AMINO ACID | |
| 1-Letter | 3-Letter | |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as NH2 or acetyl or to a carboxy-terminal group such as COOH.

"Recombinant DNA (rDNA) molecule" refers to a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

"Vector" refers to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow convenient expression of a recombinant methioninase protein of this invention.

B. DNA Segments and Vectors

1. Methioninase-Coding DNA Molecules

It has been found that by operably linking an isolated DNA molecule encoding methioninase to a promoter, particularly an RNA polymerase promoter such as the T7 RNA polymerase promoter, recombinant methioninase can be expressed at levels from about 5–75% of total cellular protein, when introduced into an appropriate host cell. Accordingly, the invention provides high-level expression modules that express high levels of recombinant methioninase when introduced into a host under appropriate conditions.

As used herein, a high-level expression module, or an expression module of the present invention, refers to a nucleic acid molecule that contains one or more expression control elements that direct the transcription and translation of an operably linked nucleotide sequence that encodes methioninase. The expression module can be an isolated nucleic acid molecule or can be present in a vector (described below).

The expression modules of the present invention contain control elements that direct the production of recombinant methioninase such that the recombinant methioninase produced represents from about 5–75% of total cellular protein, preferably more than 10% of total cellular protein. The preferred expression control elements are RNA polymerase promoters, the most preferred being the T7 RNA polymerase promoter. Other examples of RNA polymerase promoters include, but are not limited to, the Tac and Trc promoters.

A promoter is an expression control element formed by a DNA sequence that permits binding of RNA polymerase and transcription to occur. Promoter sequences compatible with a particular hosts system are known in the art and are typically provided in a plasmid vector containing one or more convenient restriction sites. Typical of such plasmids vectors are those containing the T7 RNA polymerase promoter, pT7 and pET that are available from a variety of sources such as commercial suppliers and the American Type Culture Collection.

The expression modules of the present invention further comprise a nucleic acid sequence that encodes methioninase. As used herein, a nucleic acid sequence is said to encode methioninase when the transcription and translation of the nucleic acid molecule comprising the sequence results in the production of a protein having methioninase activity. L-Methioninase (L-methionine-alpha-deamino-gammamercaptomethane-lyase or methioninase) is an enzyme that degrades methionine by deamination and dethiomethylation. Methioninase activity can be measured at least by measuring the amount of alpha-ketobutyrate formed upon cleavage of methionine. One unit (U) of methioninase is defined as an amount of enzyme that produces 1 micromole of alpha-ketobutyrate per minute from methionine under the standard assay conditions described by Ito et al., *J. Biochem.*, 22:1263–1272, 1976; and Soda, *Analyt. Biochem.* 25:228–235, 1968.

The methioninase-encoding nucleic acid sequence can comprise an unaltered sequence obtained from an organism that naturally produces recombinant methioninase, or can comprise a sequence obtained from an organism that naturally produces methioninase that has been altered to contain one or more nucleic acid or amino acid substitutions, deletions or additions.

The methioninase-encoding nucleic acid molecule, whether altered or unaltered, can be derived from any organism that naturally produces methioninase. The preferred source of the methioninase-encoding nucleic acid molecule is *Pseudomonas putida*. Example 1 discloses the isolation and sequencing of a methioninase-encoding nucleic acid molecule from *P. putida*. Other preferred sources for a methioninase-encoding nucleic acid molecule include, but are not limited to, *Trichomonas vaginalis, Nippostrongylus brasiliensis,* and Fusobacterium sp.

The complete coding sequence for methioninase can be obtained from a variety of sources, especially those recited above, using a variety of methods. The isolation of methioninase-encoding nucleic acid molecules from an organism other than *P. putida* is greatly facilitated by the amino acid and nucleic acid sequences provided in (SEQ ID NOS: 1 through 3).

Specifically, a skilled artisan can readily use the nucleic acid sequence provided in Seq. ID NO:1 to prepare pairs of oligonucleotide primers for use in a polymerase chain reaction (PCR) to selectively amplify a methioninase-encoding nucleic acid molecule from methionine expressing organisms. The preferred PCR primer pairs based on the sequence provided in SEQ ID NO:1 are:

5'-GCCGGTCTGTGGAATAAGCT-3' (Sense) (SEQ ID NO:4)
5'-CCAGGGTCGACTCCAGCGCC-3' (Antisense) (SEQ ID NO:5)

A preferred PCR denature/anneal/extend cycle for using the above PCR primers is as follows: first denaturation at 95° C. for 10 minutes, then 5 cycles of denaturation at 94° C. for 30 seconds, annealing at 60° C. for 30 seconds, and extension at 72° C. for 2 minutes; then 25 cycles of denaturation at 94° C. for 30 seconds, 60° C. for 30 seconds, then extension at 72° C. for 1.5 minutes; then final extension at 72° C. for 10 minutes. The PCR amplified products are two bands of which the 1365 bp band was collected, and purified as the insert ONCase-1 DNA.

Alternatively, a fragment of the nucleotide sequence or SEQ. ID No. 1 can be used as a probe to isolate DNA encoding methioninase from organisms other than *Pseudomonas putida* using art-known methods. Oligomers containing approximately 18–20 nucleotides (encoding about a 6–7 amino acid stretch) are prepared and used to probe genomic DNA libraries to obtain hybridization under conditions of sufficient stringency to eliminate false positives using procedures well known in the art. (See Sambrooic et al. Molecular Cloning, Cold Spring Harbor Press 1989)

DNA segments (i.e., synthetic oligonucleotides) that are used as probes or specific primers for the polymerase chain reaction (PCR), as well as gene sequences encoding methioninase, can readily be synthesized by chemical techniques, for example, the phosphotriester method of Matteucci, et al., (*J. Am. Chem. Soc.* 103:185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

In addition to PCR and DNA probe based methods, DNA molecules encoding methioninase can be isolated using polyclonal antiserum or monoclonal antibodies raised against peptide fragments of SEQ ID NO:1 that are predicted as being immunogenic. Such antibodies can be used to probe an expression library generated from a given organism, such as a lambda gt11 library, to obtain DNA molecules encoding methioninase from an organism other the *P. putida*.

Once a naturally occurring methioninase-encoding nucleic acid molecule is obtain, a skilled artisan can readily employ random or site specific mutagenesis procedures to alter the methioninase-encoding sequence so as to increase the level of expression or to substitute, add, or delete one or more amino acids from the encoded methioninase.

In one embodiment, the methioninase-encoding sequence is altered so as to increase the level of expression of the recombinant methioninase in a given host cell without changing the amino acid sequence of the encoded methioninase. Increased expression of recombinant methioninase in a particular host can be obtained by altering one or more of the codons present in the nucleic acid molecule so that the resulting codons are ones that are more frequently used by the host organism to encode a particular amino acid. Altering a nucleotide sequence to contain preferred codons can be accomplished using art known procedures such as site directed mutagenesis or by synthesizing a nucleic acid molecule containing the preferred codons.

In addition to alterations that affect expression, methioninase-encoding nucleic acid molecules can be altered so as to facilitate purification of the resulting protein. For example, as disclosed in the Examples, by altering either the amino or carboxy terminus of the recombinant methioninase so as to add a polyhistidine stretch, $Ni^{++}$ sepharose can be used to purify the resulting fusion protein.

The methioninase-encoding sequence can also be altered to introduce changes in the amino acid sequence of the encoded methioninase, so as to add, substitute, or delete one or more amino acid residues. The resulting recombinant methioninase will preferably contain alterations that result in recombinant methioninase with better biological or physiological properties such as increased activity, decreased immunogenicity, or increased serum half life. Such altered forms can be rationally designed or randomly generated.

An alteration is said to be rationally designed when the alteration is specifically chosen based on the amino acid sequence of the starting and resulting proteins and a desired physiological property. For example, one type of rationally designed alteration is to replace hydrophobic amino acids with less hydrophobic residues to increase solubility. The preferred method for generating rationally designed alterations is site direct mutagenesis using a mismatched PCR primer extension method.

Alterations are said to be randomly generated when the alteration is not rationally selected. Random mutagenesis techniques, such as chemical mutagenesis and-linker scanning mutagenesis, generate a large variety of random and non-specific alterations in a given protein encoding sequence. Such methods can be used to radically alter the methioninase-encoding nucleic acid molecule.

Altered forms of recombinant methioninase generated in this fashion are then screened for desired properties using a variety of art known methods. The choice of selection method employed will be dependent of the host, vector, and mutagenesis methods, employed as well as the properties that are selected for.

The present invention further provides vectors containing one or more of the expression modules of the present invention. Vectors are DNA molecules that are capable of autonomous replication within a host. Vectors can contain an episomal origin of replication derived from a naturally occurring plasmid, a genomic origin of replication, or can be derived from a viral genome. The choice of the vector to which an expression module of the present invention is inserted depends directly, as is well known in the art, on the functional properties desired, e.g., protein expression, and the host cell to be transformed.

In one embodiment, the vector includes a prokaryotic replicon. Prokaryotic replicons such as the ColE1 replicon, are well known in the art and can readily be employed in combination with an expression module of the present invention. In addition, the vector may include a gene encoding a selectable marker such as a drug resistance.

Eukaryotic expression vectors can also be used in combination with an expression module of the present invention. Eukaryotic cell expression vectors are well known in the art and are available from several commercial sources. Typical of such vectors are PSVL and pKSV-10 (Pharmacia), pBPV-1/pML2d (International Biotechnologies, Inc.), PTDT1 (ATCC, #31255), the vector pCDM8 described herein, and the like eucaryotic expression vectors. High level expression vectors can further be generated using insect cell expression systems such as a bacculovirus based vector system.

In general terms, the generation of a high expression module encoding methioninase typically involves the following:

First, a DNA is obtained that encodes methioninase. If the sequence is uninterrupted by introns, as expected from a bacterial source, it is suitable for expression in any host. This sequence may be altered to be in a readily excisable and recoverable form by inserting sequences containing one or more restriction endonuclease sites at regions flanking the methioninase-encoding sequence.

The excised or recovered coding sequence is then placed in operable linkage with a high expression control element, preferably in a replicable expression vector. The expression module or vector is then used to transform a suitable host and the transformed host is cultured under conditions to effect the production of the recombinant methioninase. Optionally the recombinant methioninase is isolated from the medium or from the cells; recovery and purification of the protein may not be necessary in some instances, where some impurities may be tolerated.

Each of the foregoing steps can be done in a variety of ways. For example, the desired coding sequences may be obtained from genomic fragments and used directly in appropriate hosts. The constructions of expression vectors that are operable in a variety of hosts are made using two or more appropriate replicons and control elements. Suitable restriction sites can, if not normally available, be added to the ends of the coding sequence so as to provide an excisable gene to insert into these vectors.

3. Transformed Host Cells Expressing High Levels of Recombinant methioninase

The present invention further provides host cells transformed with an expression module or vector of the present invention so as to produce from about 5–75% of total cellular protein as recombinant methioninase, preferably more than about 10% of total cellular protein. The host cell can be either a prokaryotic or a eucaryotic host.

Any prokaryotic host can be used to express the high-level methioninase-encoding modules of the present invention. The preferred prokaryotic host is *E. coli*. In the Examples that follow, the DH5a and BL21(DE3) strains of *E. coli* were used.

Preferred eucaryotic host cells include insect cells, yeast cells and mammalian cells, preferably insect cells such as SP6 and vertebrate cells such as those from a mouse, rat, monkey or human fibroblastic cell line. Other preferred eucaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eucaryotic tissue culture cell lines.

Transformation of an appropriate host with a high-level expression recombinant module of the present invention is accomplished by well known methods that typically depend on the type of host and vector used. With regard to transformation of prokaryotic host cells, electroporation or salt treatment of the host cells is preferred, for example, see Cohen et al., *Proc. Natl. Acad. Sci. USA* 69:2110, 1972; and Maniatis et al., *Molecular Cloning, A Laboratory Manual*, Cold Spring Harbor Laboratory, Cold Spring Harbor, N.Y. (1982).

With regard to transformation of eukaryotic cells, electroporation or the use of a cationic lipid is preferred, for example, see Graham et al., *Virol.* 52:456, 1973; and Wigler et al., *Proc. Natl. Acad. Sci. USA* 76:1373–76, 1979.

Successfully transformed cells, i.e., cells that contain an expression module of the present invention, can be identified by well known techniques. For example, cells resulting from the introduction of an expression module of the present invention can be cloned to produce single colonies. Cells from those colonies can be harvested, lysed and their DNA content examined for the presence of the rDNA using a method such as that described by Southern, *J. Mol. Biol.*, 98:503, 1975, or Berent et al., *Biotech.* 3:208, 1985. However, as described below, the present invention further provides a rapid screening method to identify transformants which express high levels of recombinant methioninase.

4. Identification of Hosts Expressing High Levels of Recombinant methioninase

The present invention further provides methods of identifying a transformed host cell which produces recombinant methioninase at levels from about 5–75% of total cellular protein. Specifically, it has been observed that transformed host cells expressing from about 5–75% of total cellular protein as recombinant methioninase, have a distinct and observable pink color. This is particularly pronounced when *E. coli* is used as the host.

To identify a transformed host cell expressing high levels of recombinant methioninase, a transformed cell is grown on or in a media under conditions in which the recombinant methioninase is expressed and that allows visual inspection of the growing cells. The growing cells or colonies are examined and selected based on the displaying of a pink color.

A variety of culture/growth conditions can be employed to grow transformed host cells for selection using the present methods. The components of the growth medium will depend on the nutritional requirements of the host/vector system employed and inspection system used to identify the pink color associated with high levels of recombinant methioninase expression and thereby allowing isolation of a high-level expression clone. The preferred medium is a solid medium onto which the transformed host cells can be plated and grown as isolated colonies, each of which is derived from single host. The preferred method of identifying high-level expression clones is visual inspection of growing colonies.

5. Production of Recombinant methioninase Using a High-level expression module

The present invention further provides methods for producing recombinant methioninase. Specifically, recombinant methioninase can be produced at commercially significant levels using a host transformed with one or more of the high-level expression modules of the present invention. Such a transformed host will express recombinant methioninase at a level from about 5–75% of total cellular protein. Using the hosts of the present invention, a skilled artisan can readily produce recombinant methioninase for use in a variety of diagnostic and therapeutic methods using art known methods.

The preferred method for purifying recombinant methioninase produced using a transformed host containing a high expression module encoding methioninase comprises the steps of:

a) heating an extract of a transformed cell that contains methioninase in aqueous buffers from about 40–60° C. for about 1–1.0 min., preferably 50° C. for 1 min.;

b) centrifugation of the heated extract from about 10 k to 20 k rpm in a GS-3 rotor (Sorvall, Du Pont) for about 15 min. to 1 hour, preferably at about 13K rpm for about 30 min. at 4° C.;

c) ultrafiltration of the supernatant using a filter of about 50K to 100K pore size, preferably a Millipore Pre/Scale:TFF PLHK 100 K 2.5 ft$^2$ cartridge using a 10 mM potassium phosphate buffer (pH8.3);

d) DEAE ion exchange chromatography in low ionic strength (from about 10–50 mM) KCl in a 10–20 mM potassium phosphate buffer at about pH 7.0–7.6, and collecting fractions containing methioninase eluted in a 40–200 KCl gradient, preferably using DEAE-Sepharose FF column;

e) a second DEAE ion exchange chromatography in medium ionic strength (50–100 mM) KCl in a 10–20 mM potassium phosphate buffer at about pH 8.0–8.6, and collecting fractions containing methioninase eluted in a phosphate buffer (pH 8.3) eluted in 100–200 mM KCl, preferably using DEAE-Sepharose FF column; and f) contacting said fractions collected in step (e) with a chromatography medium capable of absorbing endotoxin, and collecting the eluant, thereby removing endotoxin from said eluant to form endotoxin-free methioninase having at least 20 units methioninase activity per milligram protein and from 1–100 ng of endotoxin per mg protein, preferably using an Acticlean™ Etox column.

The cell extract is prepared from a host cell that has been altered to express high levels of recombinant methioninase (from about 5–75% of total cellular protein). For bacterial cell extracts, the extracts are generally prepared by first harvesting and washing bacterial cell cultures to form a cell paste/pellet, depending upon whether harvesting is by centrifugation or by hollow fiber filtration, which methods are generally well known.

The cells are then disrupted using conventional means. Preferably the cells are disrupted using a homogenizer, such as a cavitator-type homogenizer, for example, a Microfluidics Corp. Model #HC8000.

The resulting suspension is heated to precipitate selective proteins and other insoluble materials. Typical heating conditions are from about 45–60° C. for 1–10 minutes. Preferred is a heating step of 50° C. for 1 minute.

The heated extract is centrifuged to remove debris, and the supernatant is filtered and applied to DEAE ion-exchange chromatography medium in two steps as described above. Preferred adsorption and elution conditions are described in the Examples. Any of a variety of DEAE ion exchange column chromatography media can be used in these steps, and the choice of media is not to be construed as limiting. Commercial sources include Pharmacia Fine Chemicals, BioRad, and Sigma.

Thereafter, endotoxin is removed to produce a protein having acceptable levels of endotoxin as recited earlier. The endotoxin removal step can be carried out in any of a variety of means, as are well known, and typically involve contacting the protein in solution with a chromatography medium capable of adsorbing endotoxin, and yielding a chromatography medium eluant which contains endotoxin-free protein. The preferred commercial reagent for use in removing endotoxin is Acticlean™ Etox.

C. Therapeutic Compositions

The present invention further provides therapeutic compositions comprising a therapeutically effective amount of substantially isolated recombinant methioninase that is produced using a host transformed with a high-level expression module encoding methioninase.

The compositions of the present invention will preferable contain recombinant methioninase that has a specific activity of about 10 to 50 units (U) per mg protein. Typical preparations of purified recombinant methioninase are described herein having a specific activity of about 16 to 24 U/mg. In the Examples, recombinant methioninase prepared using the expression vector pAC-1 had a specific activity of 20.1 U/mg.

The recombinant methioninase in the compositions of the present invention is preferably substantially isolated. By substantially isolated is meant that the enzyme is at least 90% pure by weight, preferably at least 95% pure, and more preferably at least 99% pure, or essentially homogeneous. A preferred recombinant methioninase is essentially homogeneous when analyzed on electrophoretic media such as polyacrylamide gel electrophoresis (PAGE or SDS-PAGE). Homogeneous on PAGE means only a single detectable band.

The recombinant methioninase used to prepare the compositions of the present invention is preferably substantially free of endotoxins, such as bacterial lipopolysaccharides, due to the undesirable side effects associated with endotoxins when physiologically contacted in a mammal, as by i.v. or i.p. administration. By substantially free is meant less than about 10 nanograms (ng) endotoxin per milligram (mg) recombinant methioninase protein, preferably less than 1 ng endotoxin per mg recombinant methioninase, and more preferably less than 0.1 ng endotoxin per mg recombinant methioninase.

The recombinant methioninase used to prepare the compositions of the present invention is preferably prepared from a gene cloned from P. putida and expressed using a high-level expression vector as herein described.

The recombinant methioninase containing compositions of the present invention may further comprise a physiologically tolerable carrier. As used herein, the terms "pharmaceutically acceptable", "physiologically tolerable" and grammatical variations, both referring to compositions, carriers, diluents and reagents that the materials are capable of administration to or upon a mammal or human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. In addition, a therapeutic amount of recombinant methioninase can be present in a ointment or on a diffusible patch, such as a bandage, as to afford local delivery of the agent.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethyilamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein. Exemplary of such additional liquid phases are glycerin, vegetable oils such as cottonseed oil, organic esters such as ethyl oleate, and water-oil emulsions, particularly the liposome compositions described earlier.

A therapeutic composition contains an effective amount of recombinant methioninase, typically an amount of at least 0.1 weight percent of active protein per weight of total therapeutic composition, and preferably is at least about 25 weight percent. A weight percent is a ratio by weight of recombinant methioninase protein to total composition. Thus, for example, 0.1 weight percent is 0.1 grams of recombinant methioninase per 100 grams of total composition.

Insofar as a recombinant methioninase composition can be used in vivo intravascularly, it is contemplated in one embodiment to formulate a therapeutic composition for controlled delivery of the recombinant methioninase, and optionally to shield the recombinant methioninase protein from degradation and other phenomenon which would reduce the serum half-life of therapeutically administered recombinant methioninase.

Thus, in one embodiment, the invention contemplates therapeutic compositions containing delivery vehicles such as polymers, polymeric vehicles, particulates, latexes, coacervates, ion-exchange resins, liposomes, enteric coatings, mediators, bioadhesives, microcapsules, hydrogels, and the like vehicles. Exemplary drug delivery vehicles including liposomes are described at least by Tarcha in "Polymers For Controlled Drug Delivery", CRC Press, Boca Raton, 1990.

D. Chemically Modified Recombinant methioninase

The present invention further provides the recombinant methioninase of the present invention that is chemically modified, for example by conjugation to a polymer. By "chemically modified" is meant any form of recombinant methioninase that is changed to a form that is different than the recombinant methioninase purified from nature. Preferably, the recombinant methioninase is chemically modified by linking the recombinant methioninase to a polymer or to a polyalkylene oxide. Recombinant methioninase conjugated to a polymer increases the serum half-life and decreases the immunogenicity or antigenicity of the resulting compound.

Examples of polymers and polyalkylene oxide to which proteins may be attached include, but are not limited to, polyethylene glycol, particularly MSC-5000 PEG, polyethylene oxide, polypropylene oxide, copolymers of ethylene oxide, and copolymers of propylene oxide. Methods for chemically modifying proteins are well known to the art and can readily be used to modify the recombinant methioninase of the present invention, for example, see priority application PCT/US93/11311.

E. Formulations of recombinant methioninase

The present invention further provides methioninase in lyophilized or crystalline form. In detail, it has been observed that methioninase can readily be lyophilized or crystallized using art known methods. The resulting preparation of methioninase, crystallized or lyophilized forms, were found to be highly stable, readily hydratable, and remained highly active following rehydration.

A variety of art known methods can be used to obtain methioninase in crystallized or lyophilized form. In the examples, lyophilization and crystallization of methioninase were performed using a Verdis, Freeze mobile 24, at 100 milifar, −80° C. for 72 hours. A skilled artisan can readily adapt other art known procedures for use in producing lyophilized or crystallized forms of methioninase.

F. Uses for the Recombinant methioninase of the Present Invention

The recombinant methioninase of the present invention can be used in diagnostic and therapeutic methods that have been developed and described elsewhere that use methioninase purified from a natural sources, see PCT/US93/11311. For example, the recombinant methioninase of the present invention can be used 1) as an antitumor agent in a variety of modalities, such as by depleting methionine from a tumor cell, which are possibly universally methionine dependent, tumor tissue or the circulation of a mammal with cancer, so that the tumor growth will be inhibited 2) to induce cell cycle stasis in tumor cells followed by cell synchronization and the use of antimitotic agents, 3) in combination with antimitotic and cell cycle-specific cytotoxic agents, 4) to deplete cellular methionine prior to labeling with [$^{11}$C] methionine, which can be used in tumor diagnosis and localization, 5) to deplete serum homocysteine to prevent and cure cardiovascular diseases that are mediated by high serum levels of homocysteine. In the Examples that follow, the recombinant methioninase of the present invention was administered to three patients. Infusion dosage of up to 20,000 units, infused over ten hours, had no significant side effects and yielded a depletion of methionine for 10 hours following infusion. A skilled artisan will readily use the recombinant methioninase of the present invention as a substitute for recombinant methioninase derived from other sources in any art-known method of use.

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

EXAMPLE 1

Isolation of Nucleic Acid Molecules Encoding Methioninase

PCR Reaction of the Insert of Methioninase Gene Clone

Genomic DNA of *Pseudomonas putida* AC-1, derived from ATCC8209, was used as template; the primers used were as follows:

```
                                      (SEQ ID NO:4)
t1:5'-GCCGGTCTGTGGAATAAGCT-3' (Sense),
                     HindIII (SEQ ID NO:5)
t2:5'-CCAGGGTCGACTCCAGCGCC-3' (Antisense).
       Sal I
```

The PCR reaction condition was as follows: first denaturation at 95° C. for 10 minutes, then 5 cycles of denaturation at 94° C. for 30 seconds, annealing at 60° C. for 30 seconds, and extension at 72° C. for 2 minutes; then 25 cycles of denaturation at 94° C. for 30 seconds, 60° C. for 30 seconds, then extension at 72° C. for 1.5 minutes; then final extension at 72° C. for 10 minutes. The PCR amplified products are two bands of which the 1365 bp band was collected, and purified as the insert ONCase-1 DNA.

Cloning and Transformation

The ONCase-1 DNA was ligated with pT7Blue T-vector (Novagen) at the EcoR V T-cloning site. The pONCase-1 DNA was transformed into DH5-α bacterial cells using standard procedures.

DNA Sequencing

DNA sequencing was performed using T7 DNA polymerase and the dideoxy nucleotide termination reaction. The primer walking method was used. [$^{35}$S] TP was used for labeling. Sequencing reactions were analyzed on 6% polyacrylamide wedge or non-wedge gels containing 8M urea. DNA samples were loaded in the order of ACGT. DNA sequences were analyzed by MacVector. The DNA sequence and corresponding amino acid sequence are provided in FIGS. 1A–1D.

EXAMPLE 2

High Expression Clones of Recombinant Methioninase

PCR Reaction of the Insert for the Methioninase Expression Clone

The pONCase-1 clone was used as the template, the primers used are as follows:

```
t14. 5' - GGAATTCCATATGCACGGCTCCAACAAGC - 3' (Sense)              (SEQ ID NO:6)
                 NdeI t15. 5' - AGTCATCCTAGGTCACATCATCATCATCATCATGGCACTCGCCTTGAGTGC-3'  (SEQ ID NO:7)
                 BamHI    (Antisense)

t18. 5' - AGTCATCCTAGGTCAGGCACTCGCCTTGAGTGC - 3' (Antisense)      (SEQ ID NO:8)
                 BamHI
```

The PCR reaction condition was as follows: first denaturation at 95° C. for 10 minutes, then 5 cycles of denaturation at 94° C. for 1 minute, annealing at 56° C. for 1.5 minutes, and extension at 72° C. for 2 minutes; then 20 cycles of denaturation at 94° C. for 30 seconds, 56° C. for 30 seconds, then extension at 72° C. for 1.5 minutes; then final extension at 72° C. for 10 minutes. Two PCR amplified products, ONCase-2 (1238 bp), ONCase-3 (1220 bp) band were collected and purified.

Cloning and Transformation

The DNA of ONCase-2 and ONCase-3 DNA was digested with NdeI and BamHI and ligated with the pT7.7 vector at the NdeI and BamHI cloning sites. The pONCase-2 and pONCase-3 DNA sequences were then transformed into BL21 (DE3) bacterial cells using standard procedures.

Selection of pAC-1 and pAC-2 Clones

The positive clones were selected from Ampicillin-containing plates. After storage at 4° C. for 24 hours, the positive clones which expressed high level of recombinant methioninase had a distinct pink color that allowed their identification and selection. The methioninase expression levels of the positive clones were determined by activity assay. Two high expression clones were selected as the pAC-1 clone which contained ONCase-3 and as the pAC-2 clone which contained ONCase-2.

Construction of pAC-3 Clone and pAC-4 Clone

The tetracycline resistance gene was obtained from pBR322 at the Ava I and Cla I sites. The Ava I end was filled into a blunt end, and was ligated with pAC-1 which was digested with the BamH I and Cla I restriction enzymes, with the BamH I end filled into a blunt end. Positive clones which became pink after storage at 4° C. for 24 hours were selected from Tetracycline-containing plates. A high expression recombinant methioninase clone was determined by activity assay and named as the pAC-3 clone.

The Tetracycline-resistance gene was also obtained from pBR322 at the Ava I and Hind III sites. The Ava I end was filled into a blunt end, and was ligated with pAC-1 which was digested with the Hind III and Cla I restriction enzymes, with the Cla I end filled into a blunt end. Positive clones which became pink after storage at 4° C. for 24 hours were selected from Tetracycline-containing plates. A high expression recombinant methioninase clone was determined by activity assay and named as the pAC-4 clone. A variety of high level expression clones are provided in Table 1.

TABLE 1 rMETase Expression Clones

| Clone | Vector | Antibiotic Resistance | Promoter | Fusion | Expression* (g/l) |
|---|---|---|---|---|---|
| pAC-1 | pT7.7 | Amp | T7 | — | 1.0 |
| pAC-2 | pT7.7 | Amp | T7 | His. Tag | 0.5 |

TABLE 1-continued rMETase Expression Clones

| Clone | Vector | Antibiotic Resistance | Promoter | Fusion | Expression* (g/l) |
|---|---|---|---|---|---|
| pAC-3 | pT7.7 | Tc | T7 | — | 0.5 |
| pAC-4 | pT7.7 | Tc | T7 | — | 1.0 |

*Expression level in shaking flask (TB medium, 37° C., 400 rpm, 36 hours).

EXAMPLE 3

Fermentation of Recombinant Methioninase Expression Clones

The expression clones of recombinant methioninase were grown in Terrific Broth medium containing either Ampicillin (100 μg/ml) or Tetracycline (10 μg), at 28° C. or 37° C. with 400 rpm shaking in a 6-L flask or fermenter.

EXAMPLE 4

Purification of Recombinant Methioninase

An outline of the purification method is provided in FIGS. 2 and 3.

(1) Pre-column treatment of the sample

The bacteria were harvested by centrifugation at 800×g at 4° C. for 10 min. The bacterial pellet is then suspended in extraction solution (20 mM potassium phosphate pH9.0, 10 μM pyridoxal phosphate and 0.01% β-mercaptoethanol) and disrupted with a cavitator -type homogenizer (Microfluidics Corp. model #HC8000). Heat treatment of the homogenate is then carried out at 50° C. for one minute. The suspension is centrifuged with an automatic refrigerated centrifuge (SORVALL Superspeed RC 2-B) at 4° C. at 13 k rpm for 30 min. The supernatant is then collected. This step is followed by ultrafiltration by a Millipore Prep / Scale - TFF PLHK 100 k 2.5 ft² cartridge with buffer (10 mM potassium phosphate pH8.3). The pH is adjusted to 7.2 by ultrafiltration.

(2) Chromatographic conditions

The first column: DEAE Sepharose FF

Column: XK 100/60, Height: 32 cm, Volume: 2.5 L

Solution: [A] 40 mM potassium chloride, 10 mM potassium phosphate (pH7.2) containing 10 μM pyridoxal phosphate and 0.01% β-mercaptoethanol.

[B] 200 mM potassium chloride, 10 mM potassium phosphate (pH7.2) containing 10 μM pyridoxal phosphate and 0.01% β-mercaptoethanol.

Flow Rate: 5 ml/min.

Sample: About 100–200 g of total protein (10–20 mg/ml) are applied on the first column.

Gradient: [1] Pre-wash with solution A approximately 10 volumes until the $OD_{280}$ drops below 0.1.

[2] Gradient: Solution B from 20%–100%.

Fractions: Elution fractions of 200 ml are collected. The fractions containing rMETase are identified by activity assay and pooled.

The second column: DEAE Sepharose FF

Column: XK 50/30, Height: 25 cm, Volume: 500 ml

Solution: [A] 100 mM potassium chloride, 10 mM potassium phosphate (pH8.3) containing 10 μM pyridoxal phosphate and 0.01% β-mercaptoethanol.
  [B] 200 mM potassium chloride, 10 mM potassium phosphate (pH8.3) containing 10 μM pyridoxal phosphate and 0.01% β-mercaptoethanol.

Flow Rate: 5 ml/min.

Sample: Approximately 10–20 g of total protein (2–4 mg/ml), after dialysis in 100 mM potassium chloride, 10 mM potassium phosphate (pH8.3) containing 10 μM pyridoxal phosphate for 24 hours, are applied on the second column.

Gradient: [1] Pre-wash with solution A approximately 5 volumes until the $OD_{280}$ drops below 0.05.
[2] Gradient: Solution B from 0%–60%.

Fractions: Elution fractions of 200 ml are collected. The fractions containing rMETase are identified by the activity assay and pooled.

The third column: Sephacryl S-200 HR

Column: HiPrep 26/60, volume 320 ml.

Solution: 0.15 M sodium chloride in 10 mM sodium phosphate (pH7.2)

Flow Rate: 1.2 ml/ min.

Sample: Approximately 10 ml concentrated sample. (after dialysis in 0.15 M sodium chloride, 10 mM sodium phosphate (pH7.2) for 12 hours), are applied to the third column.

Fractions: Elution fractions of 20 ml containing rMETase, which are identified by yellow color and activity assay, are collected.

The fourth column: Acticlean® Etox

Purified rMETase (10–20 mg protein / ml) in a volume of 100–200 ml is applied on a 500 ml Acticlean® Etox column, and eluted with elution buffer (0.15 M sodium chloride in 10 mM sodium phosphate pH7.2) in order to eliminate endotoxin. Acticlean® Etox is reusable and can be cleaned with 1 M sodium hydroxide and can be autoclaved.

Concentration of the final eluant

The final eluant is concentrate with 30 K Amicon Centriprep Concentrators. The formulation for purified rMETase is 0.15 M sodium chloride, 10 mM sodium phosphate, pH7.2.

Purification of rMETase.Histidine: Chromatography on $Ni^{++}$ Sepharose column

The cell homogenate, after pre-column treatment, is suspended in binding buffer (5 mM imidazole, 0.5 M NaCl, 20 mM Tris.HCL, pH7.9). The column is then washed with 10 volumes of binding buffer followed by washes with 6 volumes of wash buffer (60 mM imidazole, 0.5 M sodium chloride, 20 mM Tris, HCl, pH7.9). Elution occurs after 6 volumes of elution buffer (1 M imidazole, 0.5 M NaCl, 20 mM Tris. HCl pH7.9) have been run through the column. The fractions containing rMETase, identified by yellow color, are collected.

EXAMPLE 5

Analysis for The Purity of rMETase with HPLC

Column: SUPELCO, 8-08541, Progel TM - TSK, G 3000-SWXL, 30 cm×7.8 mm.

Eluent Solution: 0.15 M sodium chloride in 10 mM sodium phosphate buffer (pH7.2).

Flow Rate: 0.1 ml/min.

Sample: 20 μl (0.1–1 mg/ml).

Figure 4B:
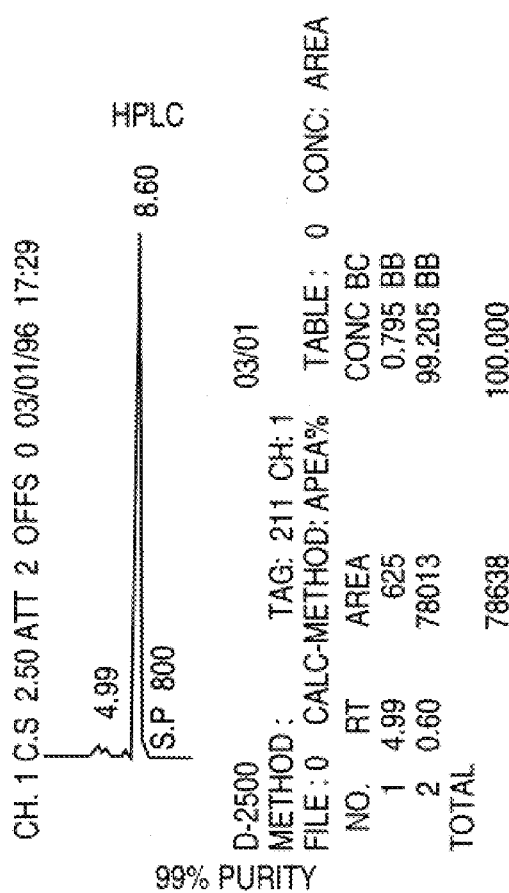

An example for production of rMETase is shown in FIGS. 2 and 3. Purity is shown in FIGS. 4A–4B.

EXAMPLE 6

Figure 5:
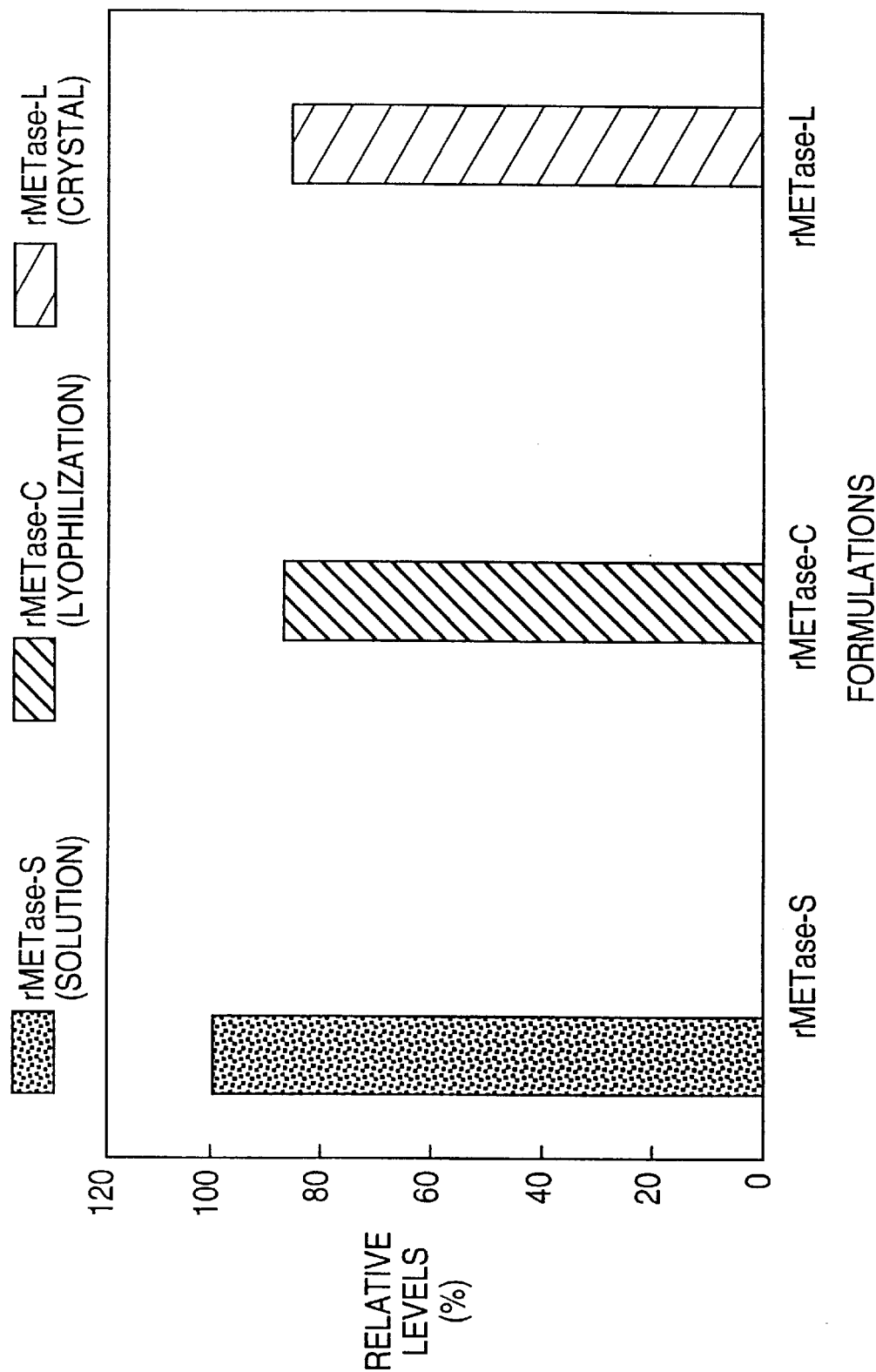
FIG. 5 provides an activity profile for different rMETase formulations.
Figure 6A:
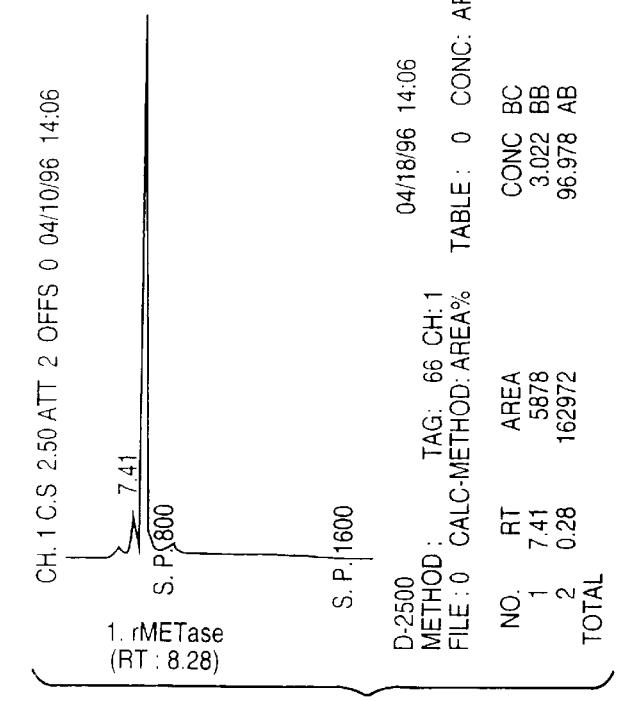
FIGS. 6A–6D provides typical purity data for PEG-rMETase.
Figure 6B:
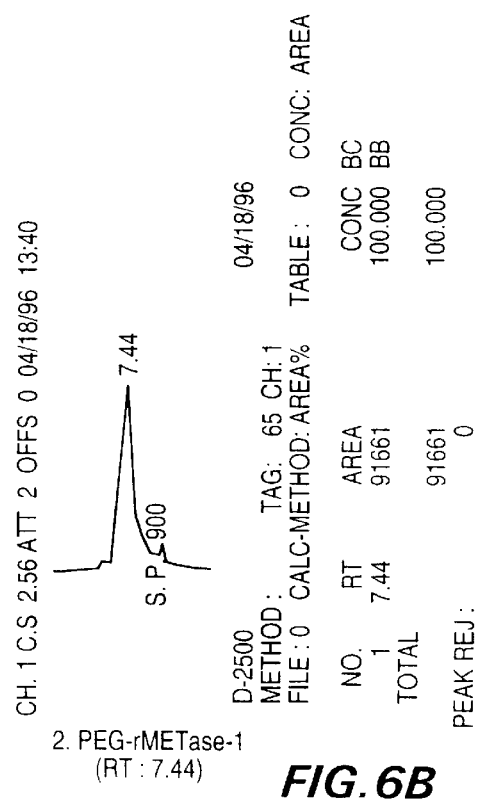
Figure 6C:
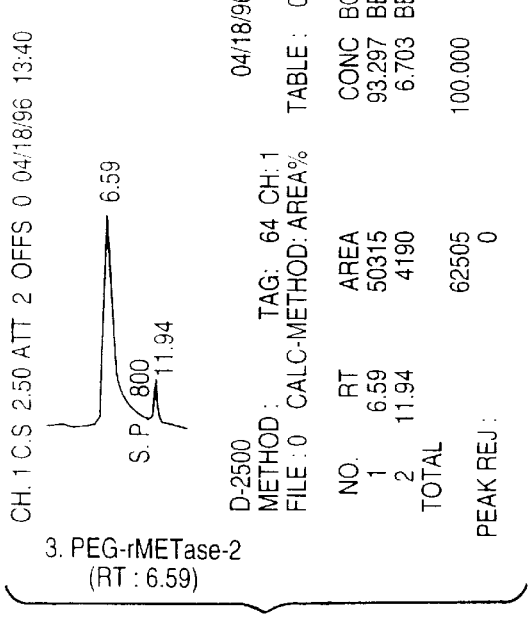
Figure 6D:
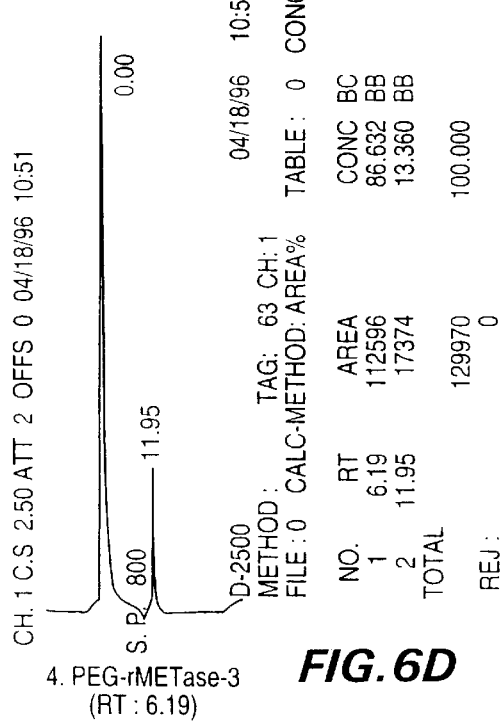

Formulations Containing Recombinant Methioninase, Crystallized and Lyophilized Forms Solution formulation:

rMETase is formulated in solution, 0.15M sodium chloride, 10 mM sodium phosphate buffer (pH 7.2), at the concentration 10–20 mg/ml. The stability of rMETase is showed in FIG. 5.

Crystallized form:

rMETase (10–20 mg/ml), in a 0.15 M sodium chloride and 10 mM sodium phosphate buffer (pH 7.2) was desalted using a Sephadex G-25 (DNA grade, superfine, Sigma) column. The solution was frozen on a dry ice and acetone bath and then crystallized in a vacuum of 100 milifar, at −80° C., for 72 hours using a Verdis Freeze Mobil 24.

Lyophilized form:

rMETase (10–20 mg/ml), in a 0.15 M sodium chloride and 10 mM sodium phosphate buffer (pH 7.2), was frozen on a dry ice and acetone bath and lyophilized in a vacuum of 100 milifar, at −80° C., for 72 hours using a Verdis Freeze Mobil 24.

Assay for activity:

The assay was carried out in a 1 ml volume of 50 mM phosphate buffer pH 8.0, containing 10 μM pyridoxal phosphate and 10 mM methionine for 10 min. at 37° C. with varying amounts of enzyme. The reaction was stopped by adding 0.5 ml of 4.5% TCA. The suspension was centrifuged at 15 K rpm for 2 min. 0.5 ml of supernatant with 0.5 ml of 0.05% 3-methyl-2-benzothiazolinone hydrazone in 1 ml of 1 M sodium acetate pH 5.2 was incubated at 50° C. for 30 min. And α-Ketobutyrate was then determined by spectrophotometry at $OD_{335}$. The amount of protein was determined by the procedure of Lowry Reagent Kit (Sigma). The specific activity was calculated as units/mg protein.

The activity of rMETase were compared, and the results showed no big difference between different formulations.

EXAMPLE 7

Chemical Modification of Recombinant Methioninase

The purified rMETase was formulated in a 0.15 M sodium chloride in 10 mM sodium phosphate buffer (pH 7.2) at a concentration between 0.1 M and 0.2 M. The activity was approximately 20 units/mg.

M-SC 5000 PEG molecular weight 5000 (Methoxy-SC-PEG, MW 5000 from Shearwater polymers Inc.), was dissolved in 20 mM sodium phosphate buffer (pH 8.3) at a concentration between 2 mM and 20 mM. The molar rations of M-SC 5000 PEG to rMETase are varied from 10:1 to 120:1.

The PEGylation reactions were carried out in reaction buffer (25 mM sodium phosphate buffer, pH 8.3), at 20° C. for 60 minutes. The reactions were stopped with stop buffer (0.14 M sodium phosphate buffer, pH 6.5) at 0° C. Unreacted M-SC 5000 PEG was then removed with 30 K Amicon Centriprep Concentrators. The resulting PEG - methioninase was formulated in 0.1 M sodium chloride and 10 mM sodium phosphate (pH 7.2) while centrifuging with 30 k Amicon Centriprep concentrators.

Analysis of PEG - rMETase in vitro

PEG-rMETase were analyzed by activity assay, electrophoresis and HPLC, FIGS. 6A–6D, FIG. 7 and FIG. 8.

Activity Assay

The activity of PEG-rMETase were between 80% to 20% of the unmodified rMETase.

Electrophoresis

PEG-rMETase were applied by both native and SDS-PAGE.

HPLC analysis:

PEG-rMETase were applied to a gel filtration column, no original rMETase peak was detected, only the PEG - METase peak were observed. The retention time (RT) were shorter along with the molecular ratios of PEG and rMETase increased.

Pharmacokinetics of PEG-rMETase

Figure 8:
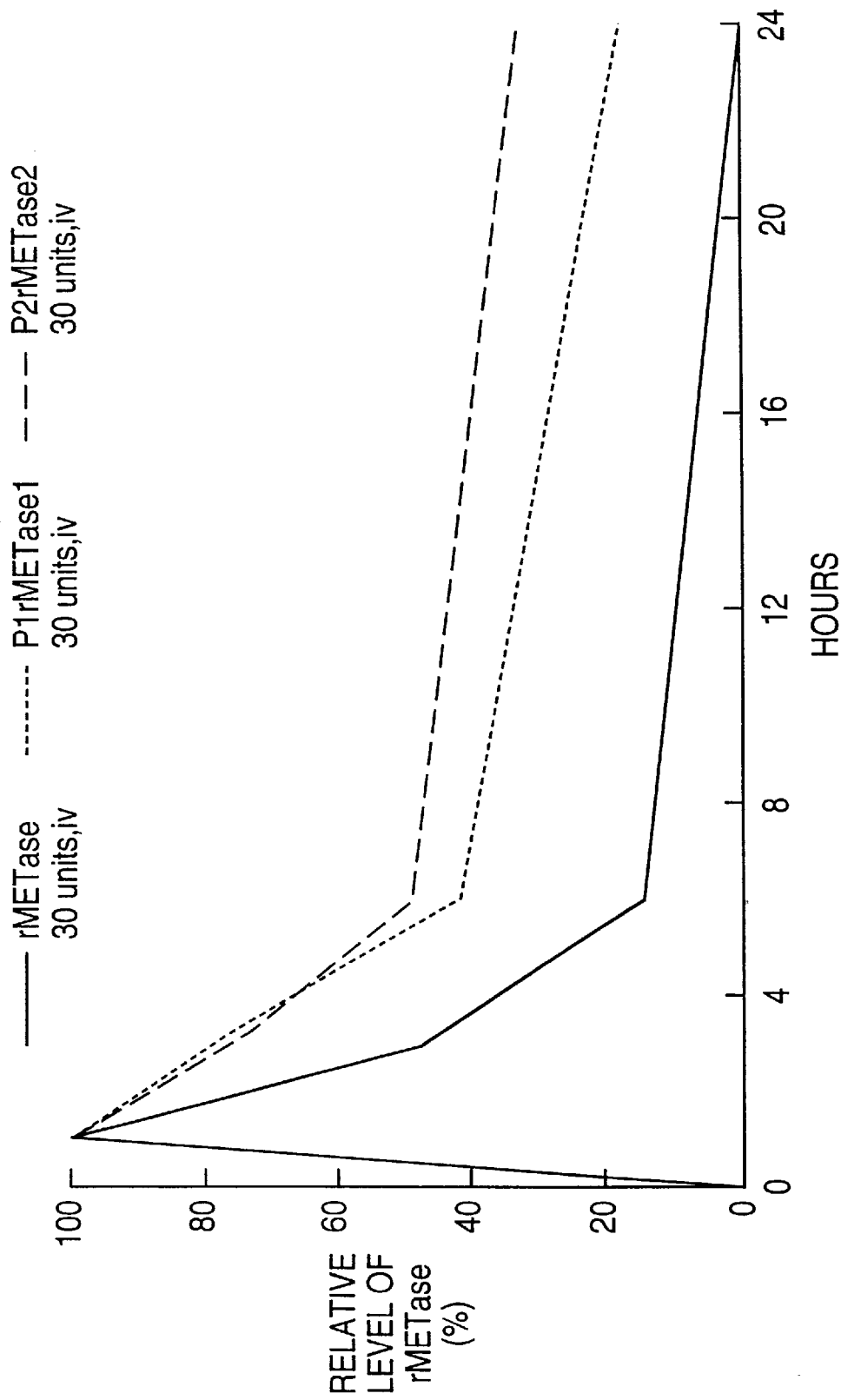
FIG. 8 provides the pharmacokinetics of PEG-rMETase in mice.

Purified endotoxin-free PEG-rMETase were injected into the tail-vein of mice. The blood samples were collected every two hours. The levels of rMETase were measured by activity assay (FIG. 8).

EXAMPLE 8

Efficacy and Toxicity of Recombinant Methioninase

1. Growth Inhibition of KB3-1 Cells by rMETase in vitro

Figure 9:
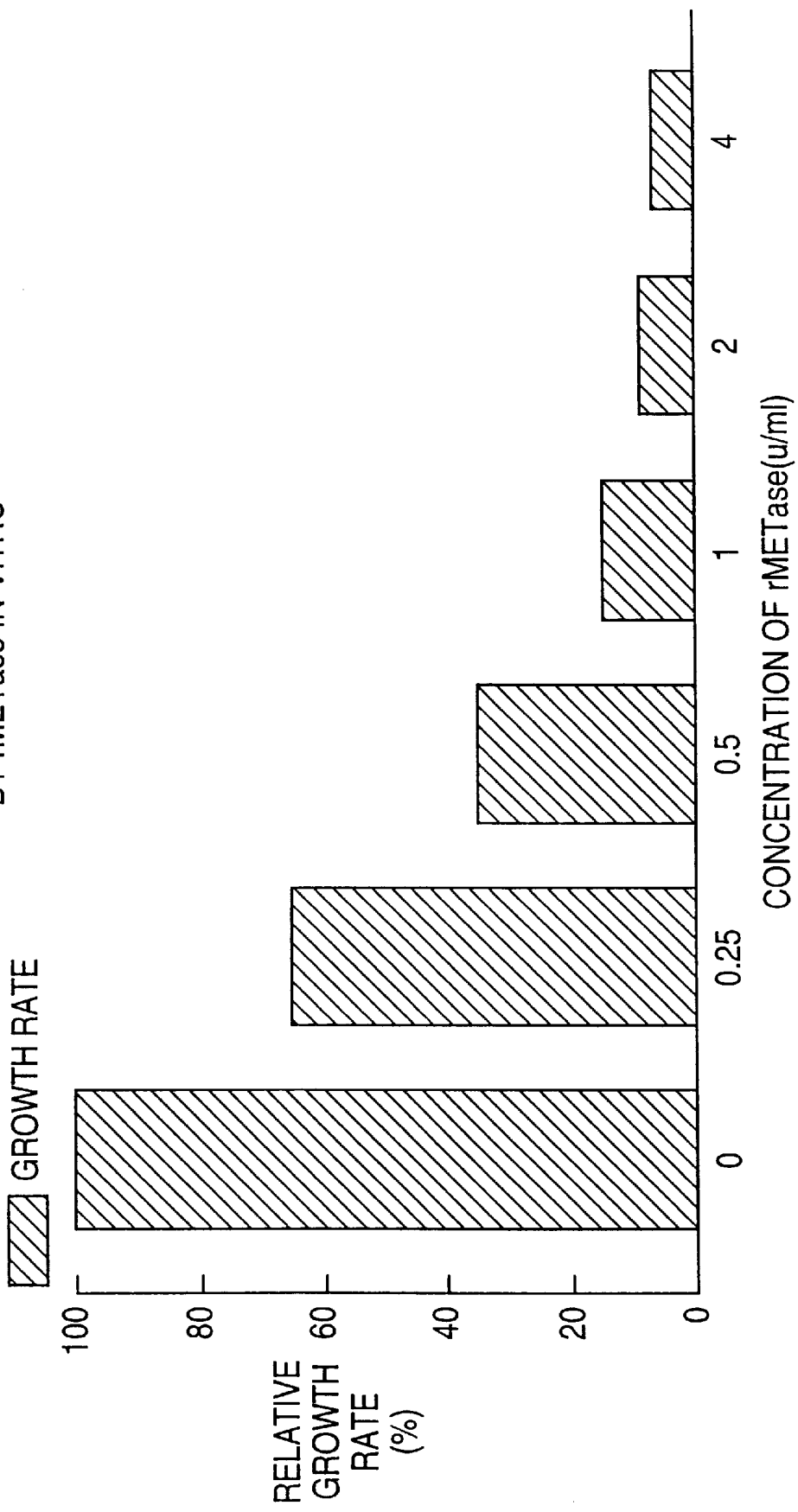
FIG. 9 provides the growth inhibition of KB3-1 cells using rMETase.
Figure 10:
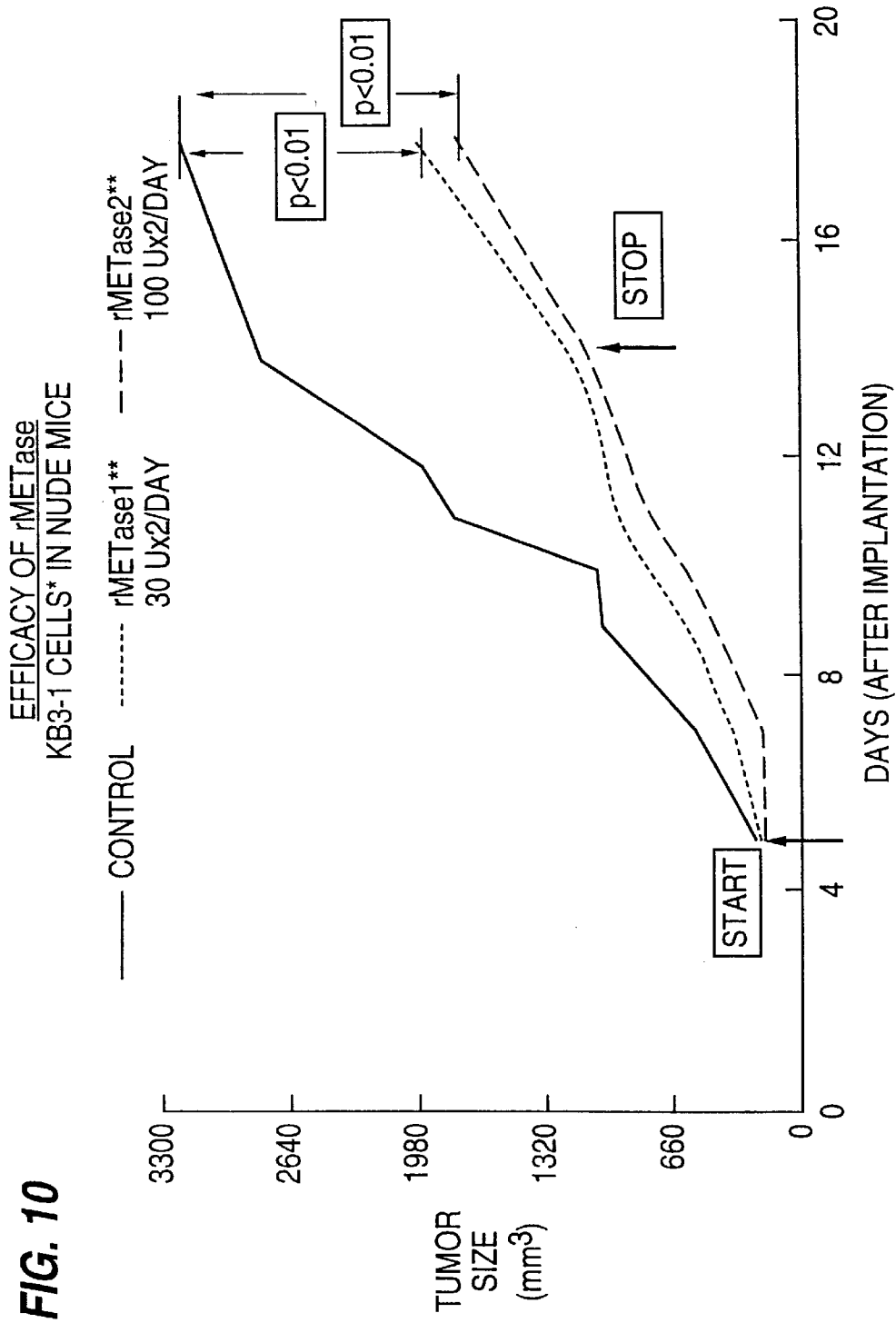
FIG. 10 provides efficacy of rMETase against KB3-1 cells in nude mice.
Figure 11:
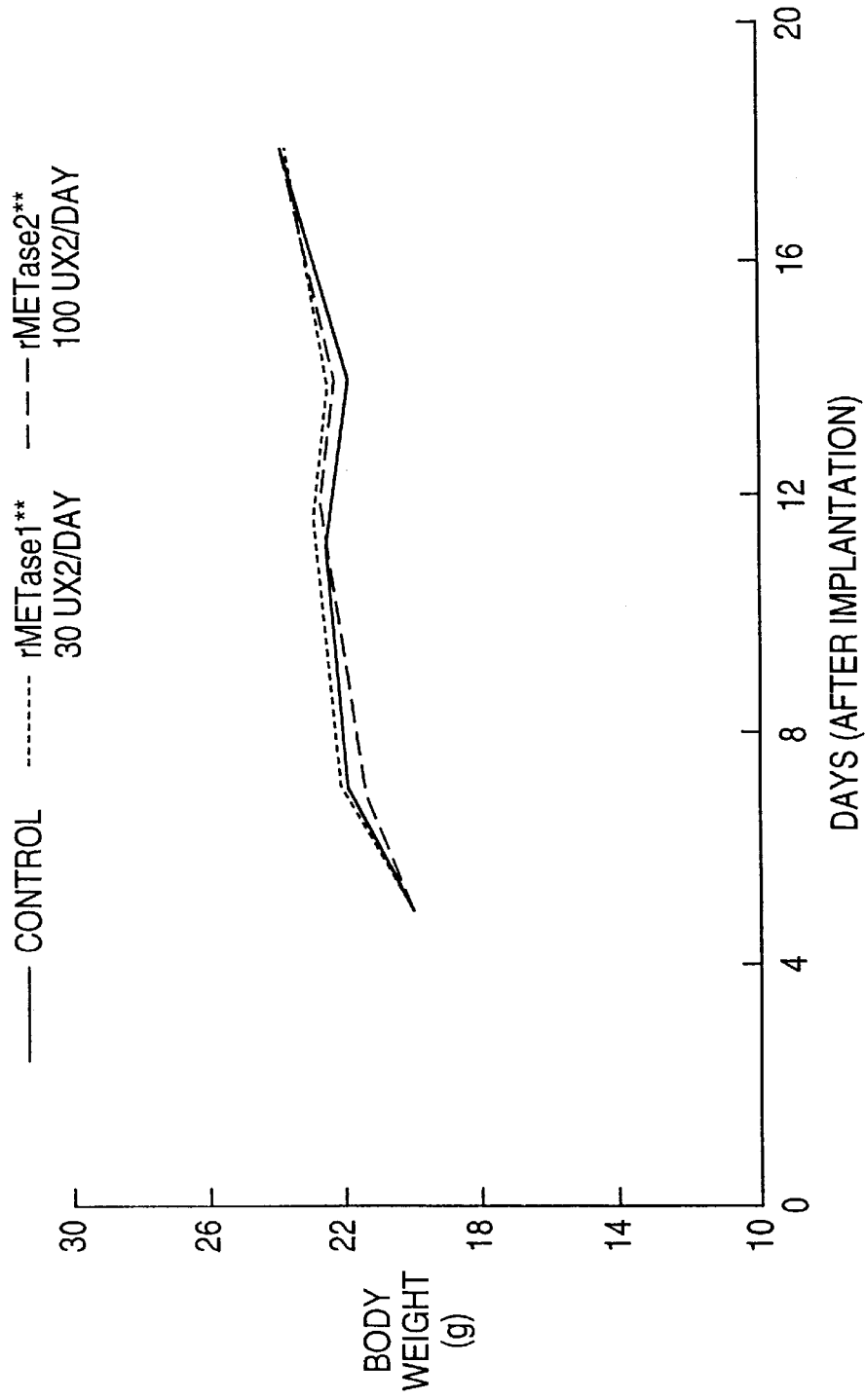
FIG. 11 provides the toxicity of rMETase in nude mice.
Figure 12:
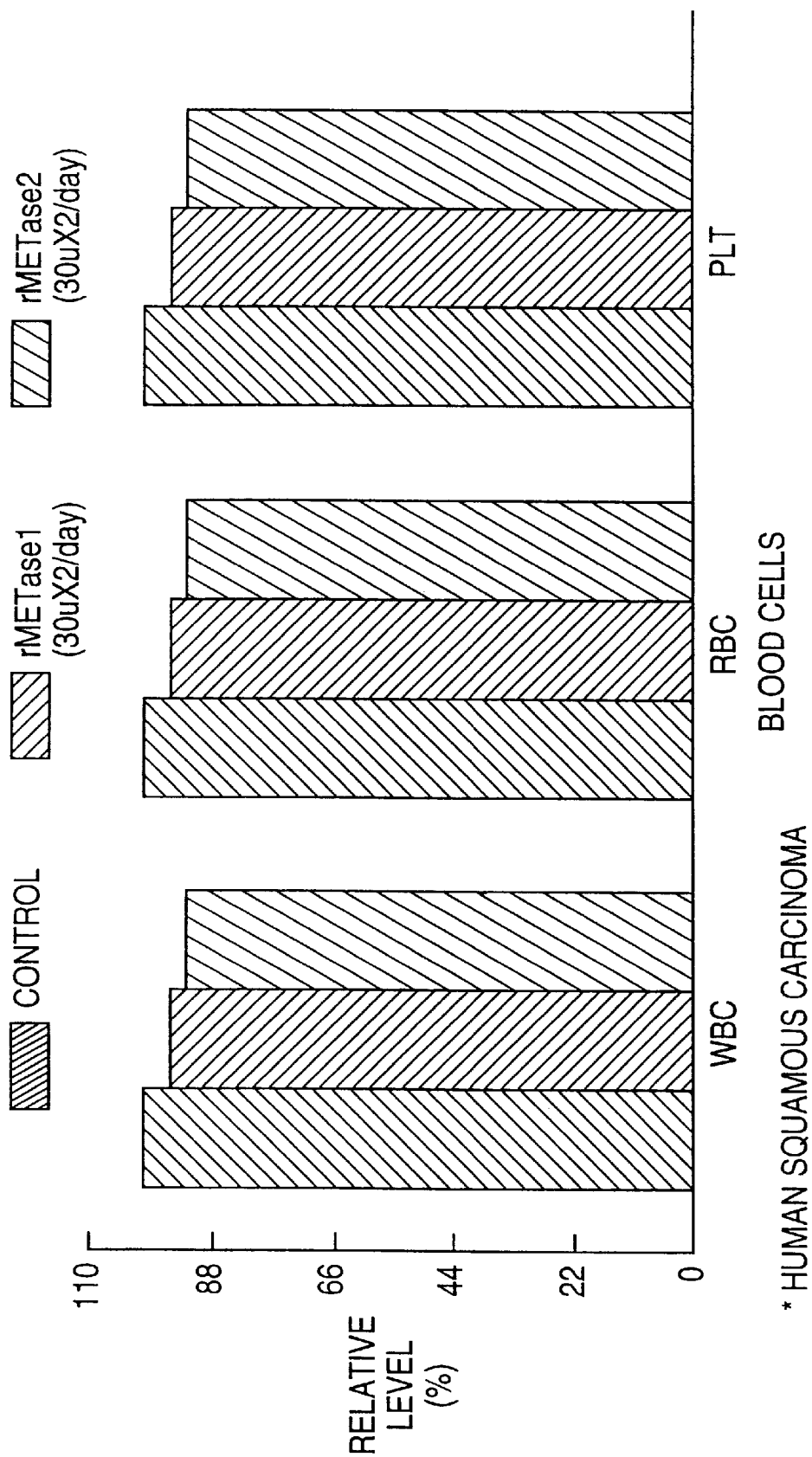
FIG. 12 provides the toxicity of rMETase in nude mice with KB3-1 cells.
Figure 13:
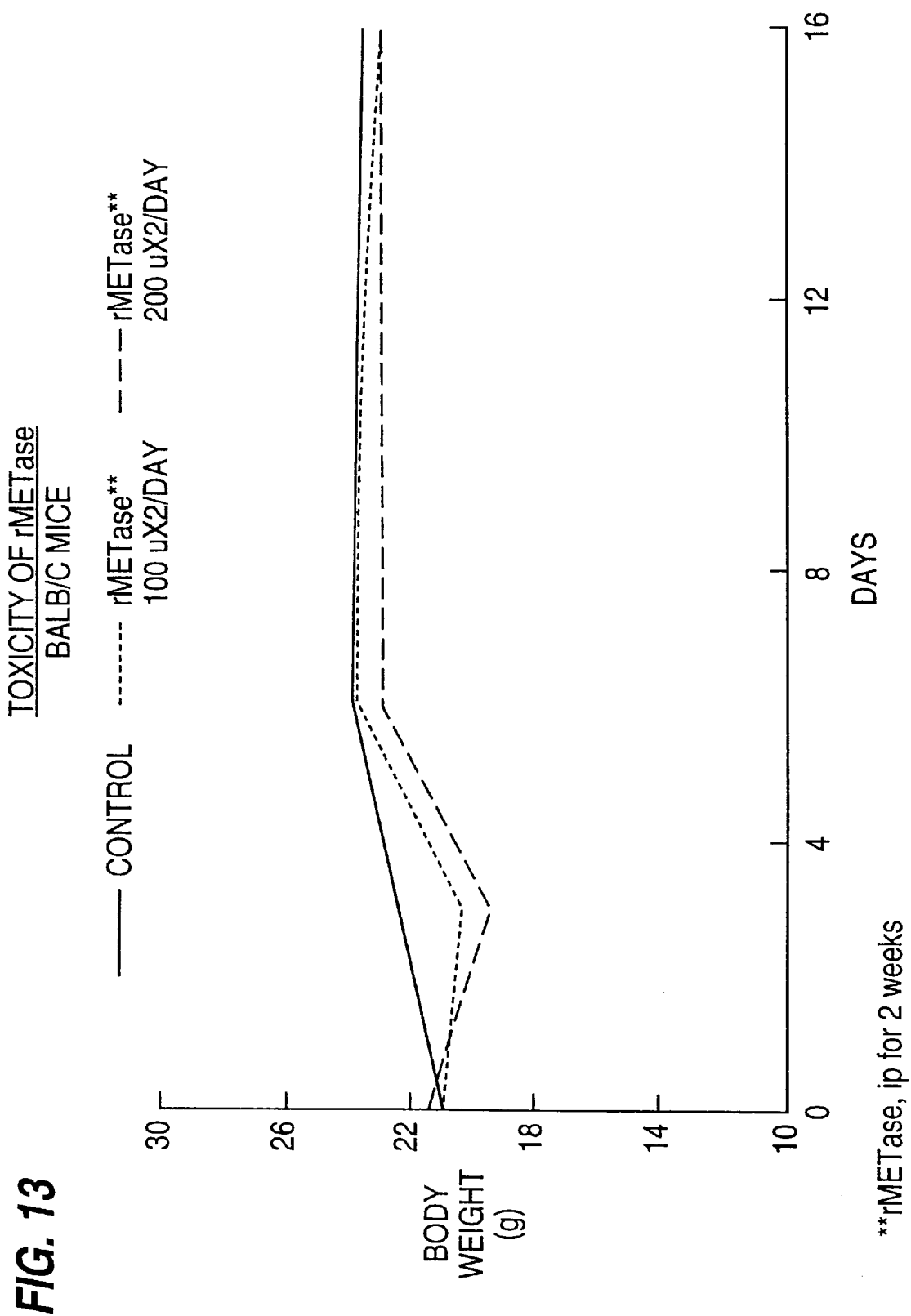
FIG. 13 provides the toxicity of rMETase in BALB/C mice.
Figure 14:
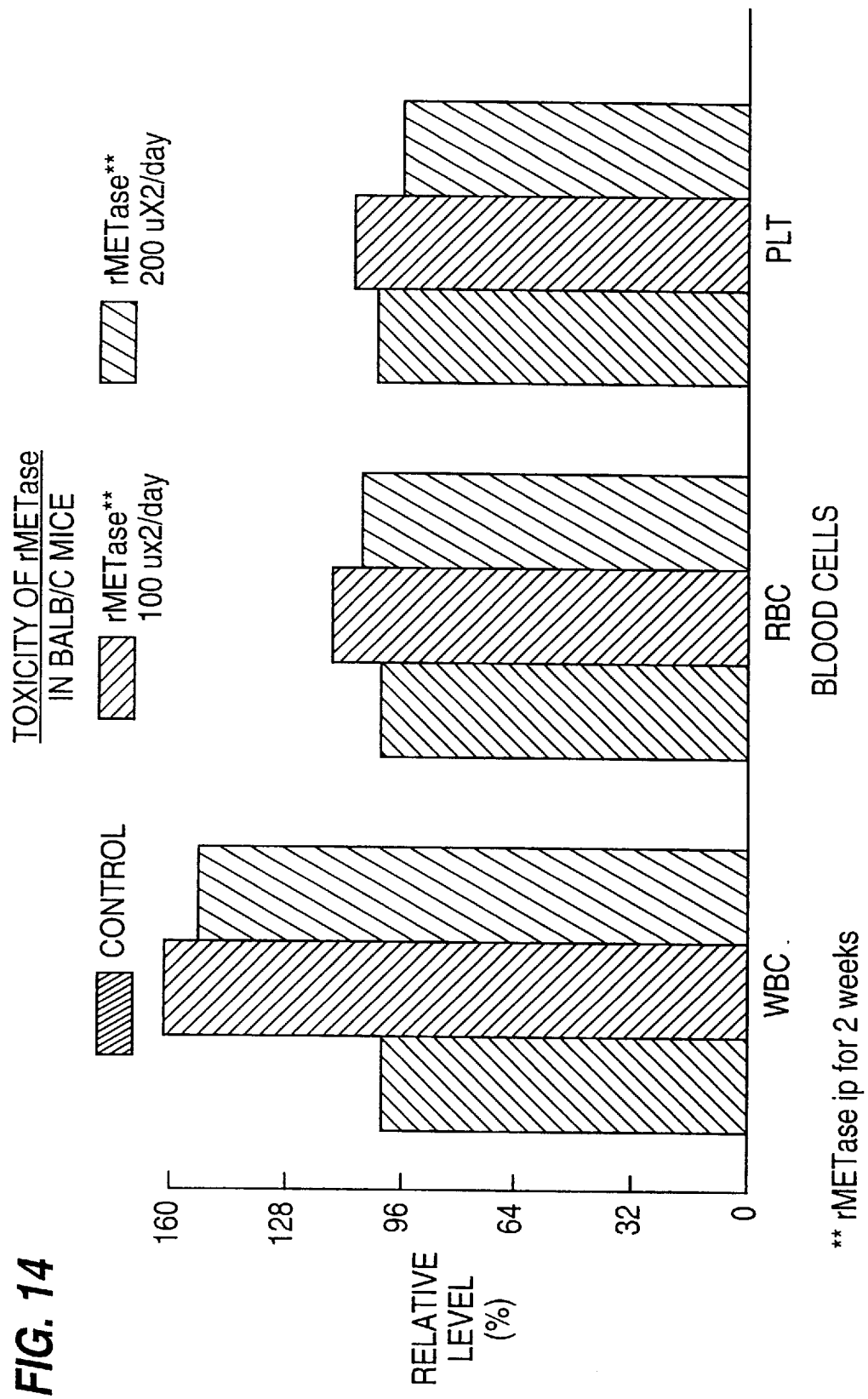
FIG. 14 provides the toxicity of rMETase in BALB/C mice.
Figure 15:
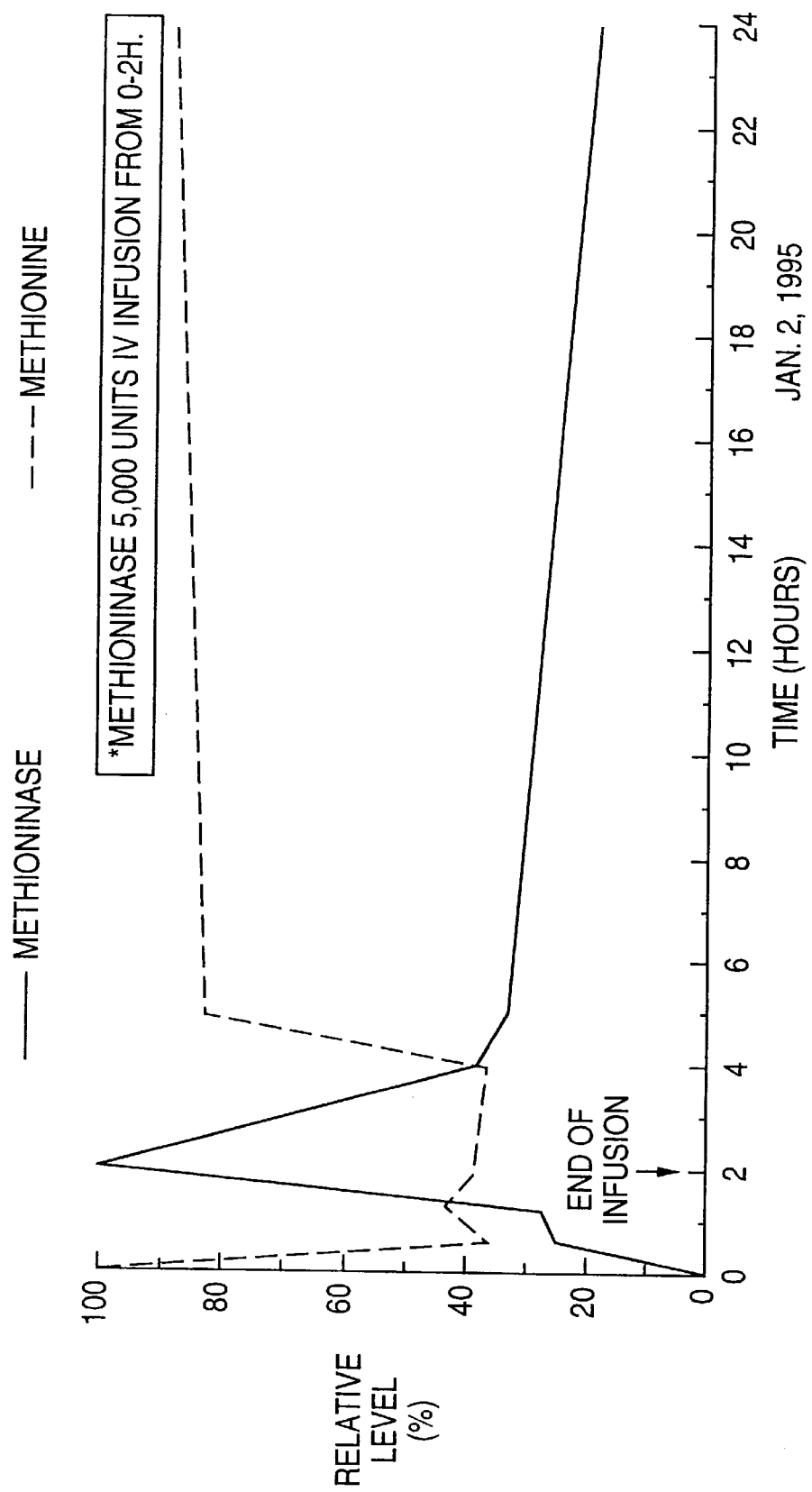
FIG. 15 provides a pharmacokinetic evaluation of methioninase in a human patient.
Figure 16:
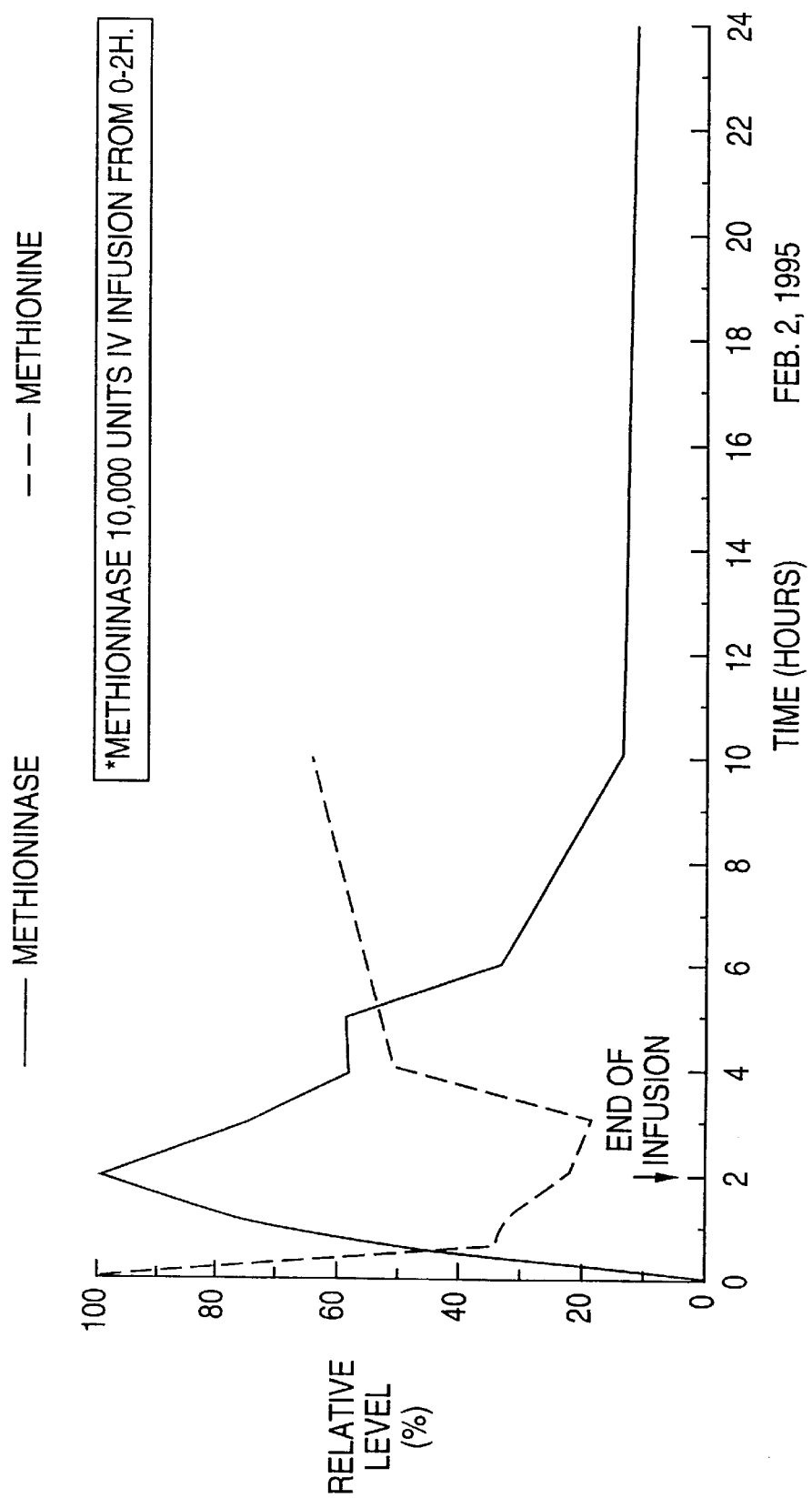
FIG. 16 provides a pharmacokinetic evaluation of methioninase in a human patient.
Figure 17:
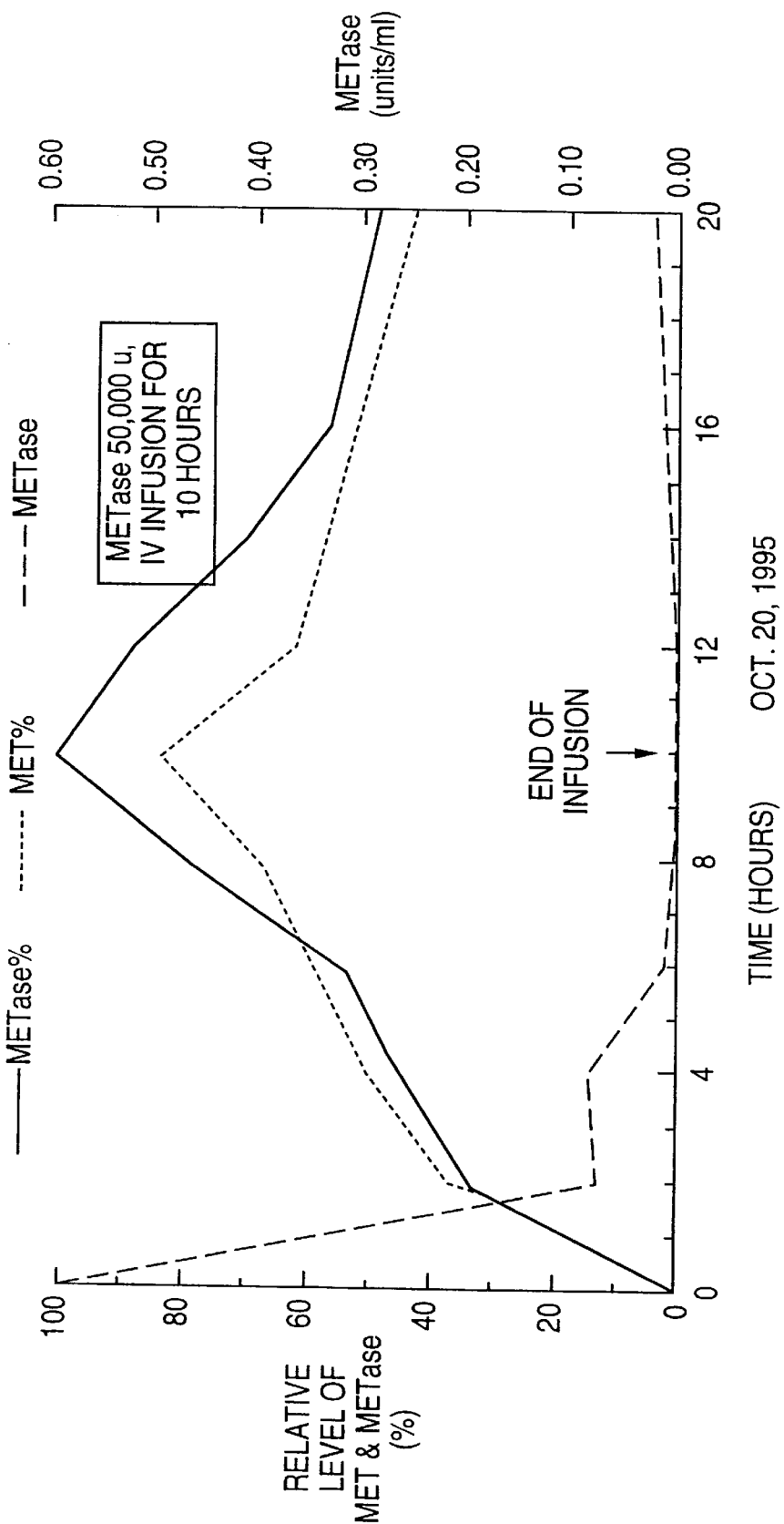
FIG. 17 provides a pharmacokinetic evaluation of methioninase in a human patient.

KB3-1 cells (Human squamous cell carcinoma) were grown in RPMI 1640 medium supplemented with 10% FBS. Various concentrations of rMETase were added to the medium and incubated at 37° C., 5% $CO_2$. The relative cell number was measured at $OD_{570}$. The results demonstrated that rMETase effectively inhibited cell growth (FIG. 9).

2. Growth Inhibition of KB3-1 Cells by rMETase in Nude mice $2 \times 10^5$ cells were injected into Balb/c nu/nu, female, mice in groups of eight. Control: normal saline. Group I: rMETasge 30 units, Group II: rMETase 100 units; ip twice a day from day 5 to day 14. The tumor size and body weight were measured. The blood was collected on day 18. The results demonstrated that rMETase effectively inhibited tumor growth without loss of body weight and effected on blood cell production (FIGS. 10–14).

3. Pilot Phase I Clinical Trial of purified, natural METase

A pilot Phase I clinical trial has been initiated in order to determine methioninase toxicity, pharmacokinetics of methioninase and methionine-depletion and maximum tolerated dose. A two hour i.v. infusion of 5,000 units (0.4 g) and 10,000 units (0.8 g) and a ten hour i.v. infusion of 20,000 units (1.6 g) of methioninase has been administered into patient-1, patient-2, and patient-3, respectively. All patients had advanced breast cancer. Blood and urine samples were obtained at frequent intervals from 0 to 24 hours. The toxicity evaluations were carried out according to WHO criteria. Pharmacokinetics data were obtained for both methioninase and methionine levels in the serum, FIGS. 15–18. No acute clinical toxicity was observed whatsoever with all toxicity criteria measured in patient-1, patient-2 and patient-3. The depletion of serum methionine started within 30 min. of the infusion, and was maintained for 4 hours after the infusion was completed in patient-1 and patient-2. The lowest serum methionine levels were 35% and 19% of the pretreatment level, respectively, in patient-1 and patient-2. Patient-3 who received a ten hour i.v. infusion of 20,000 units of recombinant methioninase without any signs of side effects maintained serum levels of recombinant methioninase as high as 50% of the maximum level for a subsequent 10 hours after infusion. Methionine was depleted over 200-fold from 23.1 $\mu$M to 0.1 $\mu$M to 10 hours of infusion. No clinical toxicity was observed whatsoever in all the toxicity criteria measured in patient-3. The results of recombinant methioninase pilot Phase I clinical trial suggested that i.v. infusion of recombinant methioninase is safe and effectively depletes serum methionine without any signs of side effects. Clinical studies are continuing to determine the maximum length of time essentially complete serum methionine depletion can be tolerated in order to proceed to efficacy studies.

4. Pilot Phase I Clinical Trial of purified, recombinant METase

Figure 19:
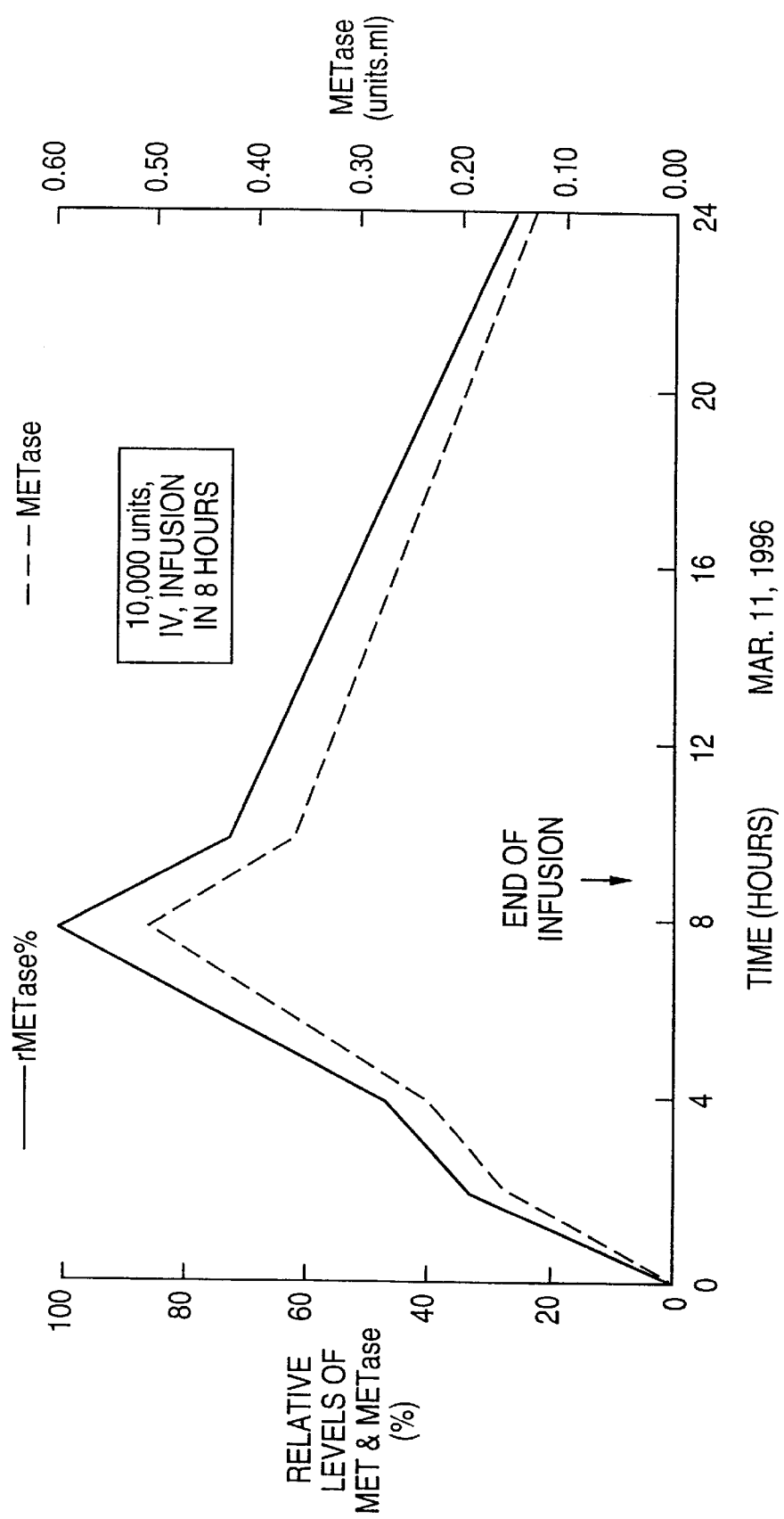
FIG. 19 provides a pharmacokinetic evaluation of rMETase in a human patient.

Patient 1, female, 50 years old, with stage IV breast carcinoma with lymph nodes metastasis, received 20,000 units (0.5 g) rMETase iv infusion for 10 hours. Physical examinations were recorded and blood samples were collected before treatment, during treatment every two hours and two hours and 16 hours after treatment. Laboratory determination were carried according to the WHO criteria. The results showed that the rMETase level was enhanced immediately after the start of the infusion, reached the highest point after 10 hours. Eight hours after the infusion was stopped the level was 50% of the peak and still maintained 20% of the peak 16 hours after the infusion. The results of the laboratory examination were evaluated according to the WHO criteria showed no acute toxicity. FIG. 19.

Patient-2, 48 years old, female, with state IV breast carcinoma with lymph nodes metastasis, received 5,000 units (0.25 g) rMETase by in infusion for 24 hours. Patient-3, 56 years old, female, with stage III renal carcinoma, received 10,000 units (0.5 g) rMETase by iv infusion for 24 hours.

Physical examinations were recorded and the blood samples were collected before treatment, during treatment every two hours and two hours and 48 hours after infusion. Laboratory determinations were carried out according to WHO criteria. The results showed that the rMETase levels were enhanced immediately after the start of the infusion and maintained high level during the infusion. After 48 hours, the methioninase level was dropped back normal.

The serum methionine levels are currently being analyzed.

The results of the laboratory examinations were evaluated, according to WHO criteria and showed no acute toxicity (Tables 2 and 3).

The result suggested that rMETase did not cause any toxicity in patient-2 and patient-3.

TABLE 2

PROTOCOL OF rMETase
CLINICAL PHASE I TRAIL

| | Patient I | Patient II | Patient III |
|---|---|---|---|
| Diagnosis | Breast cancer with metastasis | | Renal cancer |
| Sex | Female | Female | Female |
| Age | 50 | 48 | 56 |
| Methioninase | 10,000 units | 5000 units | 10,000 units |
| i.v. infusion | 8 hours | 24 hours | 24 hours |
| Blood collection | Before infusion and during infusion every two hours, After infusion 48 hours | | |
| Evaluation | WHO Criteria | | |

TABLE 2-continued

PROTOCOL OF rMETase
CLINICAL PHASE I TRAIL

| | Patient I | Patient II | Patient III |
|---|---|---|---|

AntiCancer Inc.

TABLE 3

TOXICITY OF rMETase
PILOT-CLINICAL PHASE I TRIAL)

| Physical & Laboratory Examination | Grade | | |
|---|---|---|---|
| | Patient 1 | Patient 2 | Patient 3 |
| Hematological | 0 | 0 | 0 |
| Gastrointestinal | 0 | 0 | 0 |
| Renal | 0 | 0 | 0 |
| Pulmonary | 0 | 0 | 0 |
| Fever | 0 | 0 | 0 |
| Allergic | 0 | 0 | 0 |
| Phlebitis | 0 | 0 | 0 |
| Cutaneous | 0 | 0 | 0 |
| Cardiac | 0 | 0 | 0 |
| Neurological | 0 | 0 | 0 |

*According to WHO toxicity criteria

I claim:

1. An improved methoninase formulation which formulation is detergent free and has less than one ng endotoxin per mg protein wherein said methioninase is in a form selected from the group consisting of crystalline methioninase, lyophilized methioninase, and methioninase conjugated to a polymer.

2. The formulation of claim 1 wherein said methioninase is crystalline.

3. The formulation of claim 1 wherein said methioninase is lyophilized.

4. The formulation of claim 1 wherein said methioninase is conjugated to a polymer.

5. The formulation of claim 4 wherein said polymer is polyethylene glycol (PEG).

6. The methioninase formulation of claim 5 wherein the PEG has a molecular weight of at least about 5,000.

7. The formulation of claim 1, wherein said methioninase has the amino acid sequence as depicted in SEQ ID NO:2.

8. The formulation of claim 7, wherein said methioninase is conjugated to a polymer.

9. The formulation of claim 8 wherein said polymer is polyethylene glycol.

10. The formulation of claim 7 wherein said methioninase is lyophilized.

11. The formulation of claim 7 wherein said methioninase is crystalline.

12. The methioninase formulation of claim 1 wherein said methioninase is extended with histidine residues.

13. The formulation of claim 7 wherein said methioninase is extended with histidine residues.

14. A method for making the crystallized methioninase formulation of claim 2, comprising the step of subjecting a frozen salt-free solution of methioninase to a vacuum.

15. A method for making the lyophilized methioninase formulation of claim 3, comprising the step of lyophilizing a frozen buffered, salt solution comprising from about 10 mg/ml to about 20 mg/ml of methioninase in a vacuum.

16. A method to localize a tumor in a subject which method comprises providing said subject with the methioninase formulation of claim 1 in an amount effective to deplete cellular methionine; and providing said subject with $^{11}$C-methionine to label said tumor.

* * * * *